United States Patent
Pettit et al.

(10) Patent No.: US 6,323,315 B1
(45) Date of Patent: Nov. 27, 2001

(54) DOLASTATIN PEPTIDES

(75) Inventors: George R. Pettit, Paradise Valley, AZ (US); Jayaram K. Srirangam, San Diego, CA (US); Michael D. Williams, Gilbert, AZ (US); Kieran P. M. Durkin, Folsom, CA (US); Teresa Barlozzari, Wellesley, MA (US); Andreas Kling, Mannheim (DE); Bernd Janssen, Marlborough, MA (US); Andreas Haupt, Schwetzingen (DE)

(73) Assignees: BASF Aktiengesellschaft (DE); Arizona Board of Regents, Tempe, AZ (US)

( * ) Notice: Subject to any disclaimer, the term of this patent is extended or adjusted under 35 U.S.C. 154(b) by 0 days.

(21) Appl. No.: 09/539,935

(22) Filed: Mar. 31, 2000

Related U.S. Application Data

(63) Continuation of application No. 09/394,962, filed on Sep. 10, 1999, now abandoned.

(51) Int. Cl.[7] ..................... C07D 207/09; C07D 401/02; C07D 414/02; C07K 5/083; C07K 5/103
(52) U.S. Cl. .................... 530/330; 530/331; 546/159; 546/174; 546/176; 546/187; 546/190; 546/193; 546/208; 546/223; 546/224; 546/279.1; 548/129; 548/130; 548/138; 548/152; 548/180; 548/190; 548/194; 548/195; 548/360.1; 548/490; 548/491; 548/517; 548/518; 548/530; 549/59; 549/62; 549/63; 549/65; 549/66; 549/67; 564/183; 564/186; 564/305; 564/336; 564/342; 585/21; 585/22
(58) Field of Search ..................... 530/330, 331; 548/517, 518, 530

(56) References Cited

U.S. PATENT DOCUMENTS

| | | | |
|---|---|---|---|
| 4,816,444 | 3/1989 | Pettit et al. | 514/17 |
| 5,410,024 | 4/1995 | Pettit et al. | 530/330 |
| 5,502,032 | 3/1996 | Haupt et al. | 514/17 |
| 5,530,097 | 6/1996 | Pettit et al. | 530/330 |
| 5,654,399 | 8/1997 | Sakakibara et al. | 530/330 |
| 5,663,149 | 9/1997 | Pettit et al. | 514/17 |
| 5,665,860 | 9/1997 | Pettit et al. | 530/330 |
| 5,741,892 | 4/1998 | Barlozzari et al. | 530/330 |

FOREIGN PATENT DOCUMENTS

WO 96/18408 * 2/1998 (WO).
WO 98/04278 * 2/1998 (WO).

OTHER PUBLICATIONS

Petit, G.R., et al., "The Dolastatins. 22. Synthesis of Boc-dolaproinyl–dolphenine and Four Related Chiral Isomers," et al., *J. Org. Chem.*, 59(11):2935–2938 (1994).
Petit, G.R., et al., "The Dolastatins. 17. Synthesis of Dolaproine and related Diastereoisomers," 6287–6295 (1994).
Petit, G.R., et al., "The Dolastatins. 19. Synthesis of Dolaisoleuine," et al., *J. Org. Chem.*, 59(7):1796–1800 (1994).
Petit, G.R., et al., "The Dolastatins 16. Synthesis of Dolaphenine," *Heterocycles*, 39(1):81–100 (1994).

* cited by examiner

*Primary Examiner*—Jane C. Oswecki
(74) *Attorney, Agent, or Firm*—Hamilton, Brook, Smith & Reynolds, P.C.

(57) ABSTRACT

The present invention provides compounds of the formula

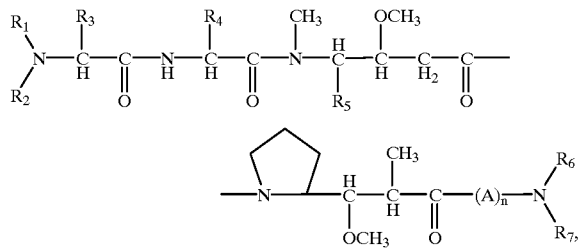

where $R_1$–$R_5$ are each, independently, a hydrogen atom or a normal or branched $C_1$–$C_6$-alkyl group; A is a methionyl, phenylalanyl or phenylglycyl residue; n is 0 or 1; $R_6$ is a hydrogen atom; and $R_7$ is a carbocyclic group, an aromatic group, a $C_1$–$C_4$-alkyl group, a pyridylalkyl group or a heterocyclic group. In another embodiment, $R_6$ is benzyl or —C(O)OR$_8$, where $R_8$ is a $C_1$–$C_6$-alkyl group, and $R_7$ is a heteroaromatic group, such as a 2-thiazolyl group.

18 Claims, No Drawings

DOLASTATIN PEPTIDES

RELATED APPLICATION

This application is a Continuation of U.S. application Ser. No.: 09/394,962, filed Sep. 10, 1999, abandoned, the entire teachings of which are incorporated herein by reference.

BACKGROUND OF THE INVENTION

A series of short peptides with significant activity as cell growth inhibitors have been isolated from the Indian Ocean sea hare *Dolabella auricularia* (Pettit et al., *J. Am. Chem. Soc.* 109: 6883–6885 (1987); Beckwith et al., *J. Natl. Cancer Inst.* 85, 483–88 (1993); U.S. Pat. No. 4,816,444; European Patent Application Publication No. 398558). These peptides are referred to as Dolastatins 1–15. Of these, Dolastatins 10 and 15 are the most potent cell growth inhibitors. Dolastatin 15, for example, inhibits the growth of the National Cancer Institute's P388 lymphocytic leukemia (PS system) cell line, a strong predictor of efficacy against various types of human malignancies. Dolastatin 10 and Dolastatin 15 effectively inhibit tubulin polymerization and growth of four different human lymphoma cell lines (Bai et al., *Biochem. Pharmacol.* 39: 1941–1949 (1990); Beckwith et al., supra (1993)).

The minute amounts of the Dolastatin peptides present in *Dolabella auricularia* (about 1 mg each per 100 kg sea hare) and the consequent difficulties in purifying amounts sufficient for evaluation and use, have motivated efforts toward the synthesis of the more promising of these compounds, including Dolastatin 10 (Pettit et al., *J. Am. Chem. Soc.* 111: 5463–5465 (1989); Roux et al. *Tetrahedron* 50: 5345–5360 (1994); Shiori et al. *Tetrahedron* 49: 1913–1924 (1993)). Synthetic Dolastatin 10, however, suffers from disadvantages which include poor solubility in aqueous systems and the need for expensive starting materials for its synthesis. These disadvantages, in turn, have led to the synthesis and evaluation of structurally modified Dolastatin 10 derivatives.

A need persists for synthetic compounds with the biological activity of Dolastatin 10 which have useful aqueous solubility and can be produced efficiently and economically.

SUMMARY OF THE INVENTION

The present invention provides compounds of the formula

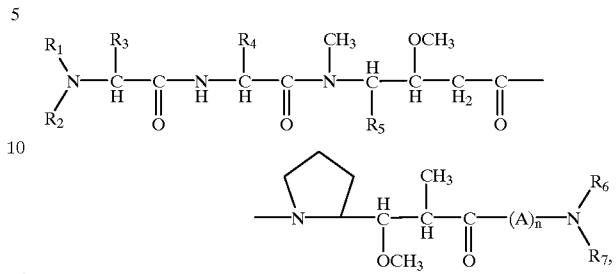

where $R_1$–$R_5$ are each, independently, a hydrogen atom or a normal or branched $C_1$–$C_6$-alkyl group; A is a methionyl, phenylalanyl or phenylglycyl residue; n is 0 or 1; $R_6$ is a hydrogen atom; and $R_7$ is a carbocyclic group, an aromatic group, a straight chain or branched $C_1$–$C_4$-alkyl group, a pyridylalkyl group or a heterocyclic group. In another embodiment, $R_6$ is benzyl or —C(O)$OR_8$, where $R_8$ is a $C_1$–$C_6$-alkyl group, and $R_7$ is a heteroaromatic group, such as a 2-tliazolyl group.

In another embodiment, the invention relates to compounds of the formula

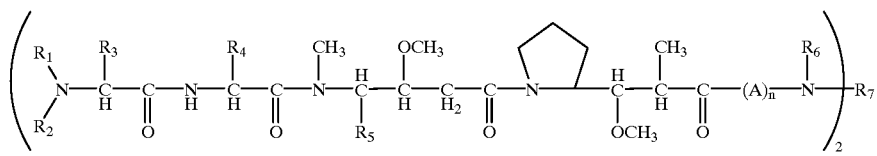

where $R_1$–$R_5$ are each, independently, a hydrogen atom or a normal or branched $C_1$–$C_6$-alkyl group; A is a methionyl, phenylalanyl or phenylglycyl residue; n is 0 or 1; $R_6$ is a hydrogen atom; and $R_7$ is an aromatic group.

In yet another embodiment, the invention provides compounds of the formula

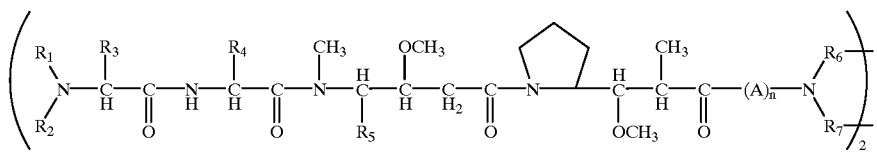

where $R_1$–$R_5$ are each, independently, a hydrogen atom or a normal or branched $C_1$–$C_6$-alkyl group; A is a methionyl, phenylalanyl or phenylglycyl residue; n is 0 or 1; and

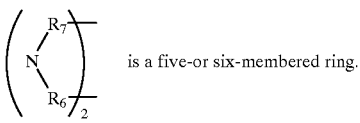

is a five-or six-membered ring.

In yet another embodiment, the present invention provides a method for treating cancer in a patient. The method comprises the step of administering to the patient a therapeutically effective amount of a compound of the invention. The invention also relates to the use of a compound of the invention for the manufacture of a medicament for treating cancer in a patient.

DETAILED DESCRIPTION OF THE INVENTION

The present invention relates to peptides having antineoplastic activity. It also includes pharmaceutical compositions comprising these compounds and methods for treating cancer in a mammal, including a human, by administration of these compositions to the mammal.

Dolastatin 10, a peptide isolated from the sea hare *Dolabella auricularia*, is a potent inhibitor of cell growth. This compound, however, is present in trace quantities in the sea hare, and is thus difficult to isolate. Dolastatin 10 is also expensive to synthesize and suffers from poor aqueous solubility. As shown herein, however, Dolastatin 10 can serve as a starting point for the development of compounds which overcome these disadvantaes while retaining antineoplastic activity or exhibiting greater antineoplastic activity than the natural product. Applicants have discovered that certain structural modifications of Dolastatin 10 provide compounds with a surprisingly improved therapeutic potential for the treatment of neoplastic diseases as compared to Dolastatin 10. Furthermore, the compounds of the present invention can be conveniently synthesized, as described below in detail.

The present invention provides antitumor peptides of Formula I,

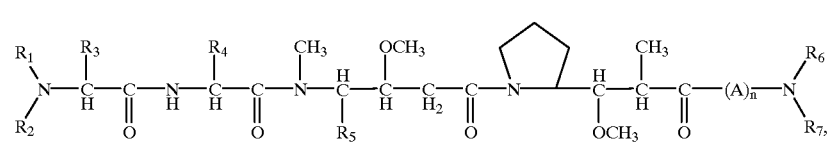

(I)

where $R_1$–$R_5$ are each, independently, a hydrogen atom or a normal or branched $C_1$–$C_6$-alkyl group. A is a methionyl, phenylalanyl or phenylglycyl residue and n is 0 or 1. In one embodiment, $R_6$ is a hydrogen atom and $R_7$ is a carbocyclic group, an aromatic group, a $C_1$–$C_4$-alkyl group, a pyridylalkyl group or a heterocyclic group. In another embodiment, $R_6$ is benzyl or —C(O)OR$_8$, where $R_8$ is a $C_1$–$C_6$-alkyl group, and $R_7$ is a heteroaromatic group, such as a 2-thiazolyl group.

The peptides of Formula I are generally composed of L-amino acids but they can also contain one or more D-amino acids. Preferred compounds of the invention are of Formula I and have the stereochemistry indicated below for a peptide of Formula I wherein n=0.

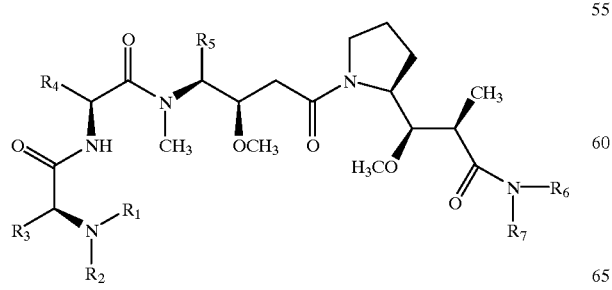

In the following discussion, compounds of Formula I have the stereochemistry shown above unless otherwise indicated.

The present compounds can also exist as salts with pharmaceutically-acceptable acids, including hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and acetylglycine.

In preferred embodiments, $R_1$ and $R_2$ are each methyl, $R_3$ is an isopropyl or sec-butyl group, $R_4$ is an isopropyl, sec-butyl or isobutyl group, and $R_5$ is sec-butyl.

In one embodiment, $R_6$ is a hydrogen atom and $R_7$ is selected from among methyl, t-butyl, isopropyl, 2-pyridylmethyl, 3-pyridylmethyl, 4-pyridylmethyl, 2-(3-pyridyl)ethyl, 4-pyridyl and groups a–r, shown below. These and other groups depicted herein are identified by the appropriate letter in Tables 1–11.

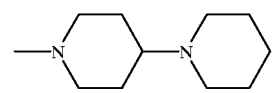
(a)

-continued

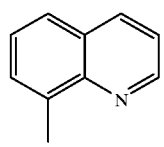
(b)

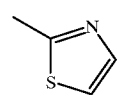
(c)

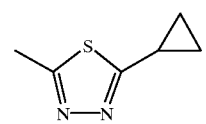
(d)

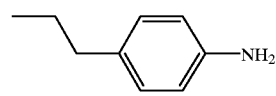
(e)

-continued (f) 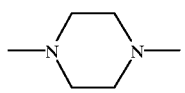

(g) 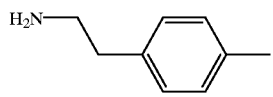

(h) 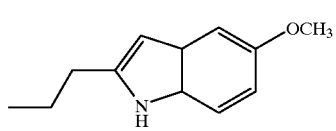

(i) 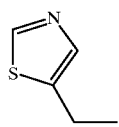

(j) 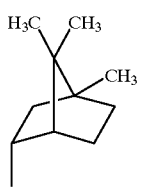

(k) 

(l) 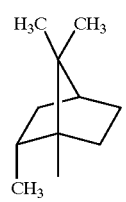

(m) 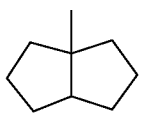

(n) 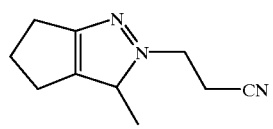

(o) 

-continued (p) 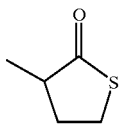

(q) 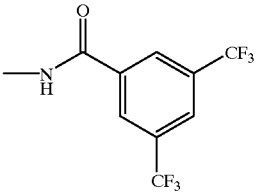

(r) 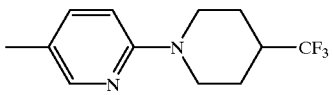

In another embodiment, $R_6$ is —C(O)OCH$_3$ or benzyl and $R_7$ is 2-tlhiazolyl.

One subset of compounds of the present invention include pentapeptides of formula I wherein $R_1$ and $R_2$ are each methyl, $R_3$ is isopropyl, $R_4$ is isopropyl, $R_5$ is sec-butyl, n is 1, A is a methionyl residue, $R_6$ is a hydrogen atom and $R_7$ is selected from among the groups j, k, m and n, shown above, and groups s, t and u, below.

(s) 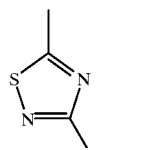

(t) 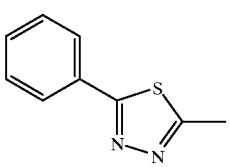

(u) 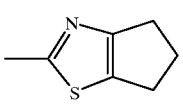

Another subset of the compounds of the present invention include tetrapeptides of Formula I in which $R_1$ and $R_2$ are each methyl, $R_3$ and $R_4$ are each isopropyl, $R_5$ is sec-butyl, n is 0, $R_6$ is a hydrogen atom and $R_7$ is selected from among t-butyl, isopropyl, methyl, 2-pyridylmethyl, 3-pyridylmethyl, 4-pyridylmethyl, 2-(3-pyridyl)ethyl, and pyryridyl, or $R_7$ is selected from among groups k, l, m, o, p, q and r.

Another subset of compounds of the present invention includes tetrapeptides of Formula I wherein $R_1$ and $R_2$ are each methyl, $R_3$ is isopropyl, $R_4$ and $R_5$ are each sec-butyl, n is 0, $R_6$ is a hydrogen atom and $R_7$ is selected from among groups s and t.

Another subset of the compounds of the present invention includes tetrapeptides of Formula I in which $R_1$ and $R_1$ are each methyl, $R_3$ is isopropyl, $R_4$ is isopropyl or sec-butyl, $R_5$ is sec-butyl, n is 0, $R_6$ is a benzyl group or —C(O)OCH$_3$ and $R_7$ is a 2-thiazolyl group.

Another subset of compounds of the invention include pentapeptides of Formula I wherein $R_1$ and $R_2$ are each methyl, $R_3$ is isopropyl, $R_4$ is isopropyl, $R_5$ is sec-butyl, n is 1, A is a phenylalanyl residue, $R_6$ is a hydrogen atom and $R_7$ is selected from among groups s and t.

The invention also provides compounds in which two peptides are linked. In one embodiment, $R_7$ is a bridging group, for example an aromatic group or an arylalkyl group, which links the C-terminal amide nitrogen atoms of two peptides as shown below.

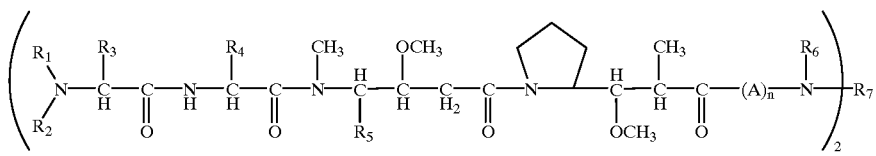

In this formula, $R_1$–$R_6$, A and n are as defined in Formula I above. Suitable examples of $R_7$ in such compounds groups u and v, shown below.

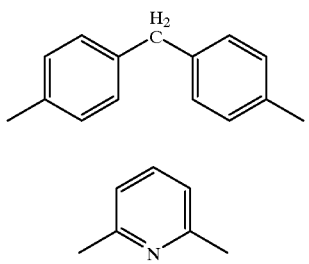

(v)

(w)

In another embodiment, the invention provides compounds of the formula

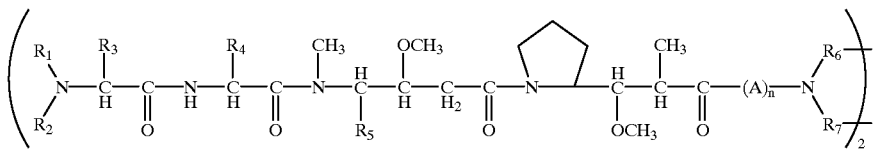

wherein $R_1$–$R_5$, A and n are as defined in Formula I and $R_6$, $R_7$ and the C-terminal amide nitrogen atoms of two peptides form a five or six-membered ring. For example, $R_6$ and $R_7$ can each be a methylene group. In this case, the two C-terminal amide nitrogen atoms are linked by two ethylene groups.

The compounds of the invention can be synthesized using conventional methods of synthetic peptide chemistry, as described in the Examples and depicted in Schemes I–VIII. For example, synthesis of the pentapeptides of the invention can proceed via an amino acid amide of the formula A—N($R_6$)$R_7$, where A is methionine, phenylalanine or henylglycine, which can be prepared by coupling the N-Boc (Boc=t-butoxycarbonyl) protected amino acid with the appropriate primary or secondary amine. The resulting amino acid amide can then be deprotected with trifluoroacetic acid and coupled with N-Boc-dolaproine to produce the corresponding dipeptide amide. The dipeptide amide can then be deprotected with trifluoroacetic acid and the resulting trifluoroacetate salt of the free amine can be coupled with an appropriate tripeptide trifuoroacetate salt.

The tetrapeptides of the invention can be prepared via a similar route. N-Boc-dolaproine can be reacted with an appropriate primary or secondary amine to form a N-Boc-dolaproine amide. The N-Boc-dolaproine amide can then be deprotected with trifluoroacetic acid, and the resulting trifuoroacetate salt of the free amine can be coupled with the appropriate tripeptide trifluoroacetate salt.

The coupling reactions can be performed by treating the peptides with a coupling agent, such as EDC with dimethylaminopyridine, ethyl chloroformate with N-methylmorpholine, or diethyl phosphorocyanidate with triethylamine. The coupling reactions are generally performed in an inert solvent, such as dichloromethane or tetrahydrofuran. The reaction temperature is typically from about −10° C. to room temperature, preferably about 0° C. The segments to be coupled are generally reacted in about equimolar amounts. About 1 to 1.2 equivalents of the coupling agent can be used, in combination with about 2 to about 4 equivalents of the amine. The deprotection of the N-Boc group can be performed with an acid, such as trifluoroacetic acid, in an inert solvent, such as dichloromethane.

In another embodiment, the present invention comprises a method for partially or totally inhibiting formation of, or otherwise treating (e.g., reversing or inhibiting the further development of) solid tumors (e.g., tumors of the lung, breast, colon, prostate, bladder, rectum, or endometrial tumors) or hematological malignancies (e.g., leukemias, lymphomas) in a mammal, for example, a human, by administering to the mammal a therapeutically effective amount of a compound or a combination of compounds of Formula I. The compound(s) may be administered alone or in a pharmaceutical composition comprising the compound(s) and an acceptable carrier or diluent. The compound or compounds of Formula I can also be administered in combination with one or more additional therapeutic agents, such as anti-cancer chemotherapeutic agents. The compound or compounds of Formula I can be administered simultaneously with the additional agent(s), or the administration of the compound(s) of Formula I and the additional agent(s) can be offset by a suitable period of time, such as hours. Administration can be by any of the means which are conventional for pharmaceutical, preferably oncological, agents, including oral and parenteral means, such as subcutaneously, intravenously, intramuscularly and intraperitoneally, nasally or rectally. The compounds may be administered alone or in the form of pharmaceutical compositions containing a compound or compounds of Formula I together with a pharmaceutically accepted carrier appropriate for the desired route of administration. Such pharmaceutical compositions may be combination products, i.e., they may also contain other therapeutically active ingredients.

The dosage to be administered to the mammal, such as a human, will contain a therapeutically effective amount of a compound described herein. As used herein, a "therapeutically effective amount" is an amount sufficient to inhibit (partially or totally) formation of a tumor or a hematological malignancy or to reverse development of a solid tumor or other malignancy or prevent or reduce its further progression. For a particular condition or method of treatment, the dosage is determined empirically, using known methods, and will depend upon factors such as the biological activity of the particular compound employed; the means of administration; the age, health and body weight of the recipient; the nature and extent of the symptoms; the frequency of treatment; the administration of other therapies; and the effect desired. A typical daily dose will be from about 0.05 to about 50 milligrams per kilogram of body weight by oral administration and from about 0.01 to about 20 milligrams per kilogram of body weight by parenteral administration.

The compounds of the present invention can be administered in conventional solid or liquid pharmaceutical administration forms, for example, uncoated or (film-) coated tablets, capsules, powders, granules, suppositories or solutions. These are produced in a conventional manner. The active substances can for this purpose be processed with conventional pharmaceutical aids such as tablet binders, fillers, preservatives, tablet disintegrants, flow regulators, plasticizers, wetting agents, dispersants, emulsifiers, solvents, sustained release compositions, antioxidants and/or propellant gases (cf. H. Sücker et al.: *Pharmazeutische Technologie*, Thieme-Verlag, Stuttgart, 1978). The administration fonns obtained in this way typically contain from about 1 to about 90% by weight of the active substance.

The present invention will now be illustrated by the following examples, which are not to be considered limiting in any way.

EXAMPLES

Example 1

Synthesis of N-Boc Amino Acid Amides, 3a–e
General Procedure A

To a solution of N-Boc amino acid 1 (4.01 mmol) in anhydrous dichloromethane (20 mL) was added at −10° C., under argon, triethylamine (4.01 mmol, 1.0 equiv.), followed by ethylchloroformate (4.01 mmol, 1.0 equiv.). After stirring at −10° C. for 40 min, the amine (2, 4.01 mmol, 1.0 equiv.) in anhydrous dichloromethane (20 ml) was added and the stirring continued at −10° C. for an additional 1 hr. The solvent was removed in vacuo and replaced by ethyl acetate and the triethylamine hydrochloride salt was removed by filtration. The filtrate was concentrated under reduced pressure and the residue subjected to flash chromatography using suitable eluents to obtain the required amino acid amides 3.

Synthesis of N-tert-Butoxycarbonylmethionine 1-amino-bicyclo[3.3.0]octane Amide

Reaction of N-Boc-L-methionine (1.0 g, 4.01 mmol, 1.0 equiv.) with 1-aminobicyclo[3.3.0]octane (2d) following General Procedure A gave, following isolation, a residue which was subjected to silica gel column chromatography (hexane:ethyl acetate, 1:1) to yield a colorless solid which was recrystallized from dichloromethane/n-hexane to afford the required product as colorless needles (3d, 900 mg, 63%); $[\alpha]^{25}_D = -11.5°$ (c 1.42, $CHCl_3$); mP 152–153° C.; IR(film): 3304, 3067, 1684, 1651 $cm^{-1}$; $^1H$ NMR (300 MHz, $CDCl_3$) δ:1.26 (2H, sextet, J 6.1, 12.18 Hz), 1.44 (9H, s, Boc), 1.60 (4H, pentet, J 6.7 Hz), 1.76 (2H, pentet, J 6.7, 5.55 Hz), 1.89–2.07(6H, m), 2.11 (3H, s, SMe), 2.32(1H, heptet), 2.54 (2H, m), 4.14(1H, q), 5.19(1H, brd, NH), 6.30(1H, s, NH); MS(m/z): 356($M^+$, 5%), 300, 282, 226, 149, 119, 104 and 57 (100%).

TABLE 1

Physical constants and spectroscopic data for the Boc-amino acid amides 3a–e

| no. | R | $R_7$ | yield % | mp ° C. | $[\alpha]_D^{25°}$, $CHCl_3$ | ir, $v_{max}$, $cm^{-1}$ | $^1H$ nmr, δ | ms $M^+$ |
|---|---|---|---|---|---|---|---|---|
| 3a | $(CH_2)_2SMe$ | k | 83 | oil | −5.3 (c 1.78) | 3297 1690 1680 1659 | 1.10(2H, q), 1.27–1.58(7H, m), 1.47(9H, s), 1.89(4H, m), 2.04(1H, m), 2.11(3H, s), 2.27(2H, m), 2.55(2H, m), 4.21(2H, m), 5.21(1H, brd), 6.25(1H, brd) | 382 |
| 3b | $(CH_2)_2SMe$ | j | 93 | 89–93 | −49 (c 1.44) | 3329 1692 1659 | 0.83(3H, s), 1.1–1.31(2H, m), 1.44(9H, s), 1.56(2H, m), 1.65–1.75(2H, m), 1.85(1H, dd), 1.87–2.15(2H, m), 2.11(3H, s), 2.56(2H, m), 3.87(1H, dt), 4.18(1H, q), 5.16(1H, brd), 6.29(1H, brd) | 384 |
| 3c | $(CH_2)_2SMe$ | n | 44 | 177–178 | −47 (c 0.29) | 3333 3281 2284 1676 | 1.46(9H, s), 2.04(1H, m), 2.14(3H, s), 2.21(1H, m), 2.37(2H, m), 2.57–2.71(6H, m), 2.88(2H, t), 4.18(2H, t), 4.38(1H, q), 5.20(1H, d), 8.23(1H, brs) | 407 |
| 3e | Ph | Ph | 85 | 134–135 | −105 (c 0.53) | 3329 1686 1663 | 1.43(9H, s), 5.33(1H, brs), 5.79(1H, brs), 7.08(1H, t), 7.24–7.46(9H, m), 7.74(1H, s) | 326 |

Example 2

Deprotection of N-Boc-Amino Acid Amides 3a–e
General Procedure B

A solution of the Boc-amino acid amide 3a–e (1.0 mmol) in dry dichloromethane (10 ml)/trifluoroacetic acid (2.0 ml) was stirred at 0° C. for 3 hr under argon. The solvent was removed in vacuo and the reside dried under high vacuum for 2 hr. The oily trifluoroacetate salts 4a–e obtained were used without further purification in the coupling reaction.

Example 3

Synthesis of Dipeptide Amides 6a–e
General Procedure C

The amino acid amide trifluoroacetate salt 4 (1.0 mmol) was dissolved in anhydrous dichloromethane (15 ml) and the solution cooled to 0° C. Triethylamine (10.7 mmol, 11 equiv.) was added followed by diethyl phosphorocyanidate (DEPC, 1.2 mmol, 1.2 equiv.) and the mixture was stirred for 2–8 hr at 0° C. The solvent was removed in vacuo and the residue was purified by silica gel flash chromatography to yield the respective dipeptide amides 6a–e.

Synthesis of N-tert-butoxycarbonyl-dolaproine-methionine 1-aminobicyclo[3.3.0]octane Amide, 6d Reaction of the trifluoroacetate salt 4d with Boc-dolaproine (5) using General Procedure C gave a residue which was purified by silica gel flash chromatography (hexane-ethyl acetate-methanol, 2:2:0.1) to afford a colorless solid (6d, 41%); $[\alpha]_D^{25}=-49°$ (c 0.82, CHCl$_3$); IR(film): 3285, 2949, 2868, 1694, 1640, 1549, 1397, 1173, 1105 cm$^{-1}$; $^1$H NMR (300 MHz, CDCl$_3$) δ: 1.24(5H, m), 1.48(9H, s, Bu$^t$), 1.59(4H, m), 1.74(4H, m), 1.93(8H, m), 2.11(3H, s), 2.31(2H, m), 2.49(1H, m), 2.60(1H, m), 3.19–3.27(1H, m), 3.40 and 3.55(1H, m), 3.43(3H, s), 3.76(1H, m), 3.85(1H, m), 4.45(1H, m), 6.44(1H, brs), 6.58 and 6.81(1H, brs); MS(m/z): 525(M$^+$4%), 493, 451, 419, 408, 393, 356, 341, 312, 210, 171, 154, 139 and 115 (100%).

Example 5

Synthesis of Boc-Dolaproine Amides 9a–g
General Procedure E

To a solution of N-Boc-dolaproine 5 (1.74 mmol, 1.0 equiv.) in anhydrous THF (20 ml) cooled to 0° C., was added 1-hydroxybenzotniazole (1.74 mmol, 1.0 equiv.), triethylamine (0.24 ml, 1.74 mmol, 1.0 equiv.) and 1-ethyl-3-(3-dimethylaminopropyl)carbodiimide (EDC, 1.74 mmol, 1.0 equiv.) and the reaction mixture was stirred at 0° C. for 1 hr. The amine (8, 1.74 mmol, 1.0 equiv.) was added and the reaction was stirred at 0° C. for 1 hr and at room temperature for 12 hr. Ethyl acetate (50 ml) was added and the solution was sequentially washed with aqueous sodium bicarbonate (7%, 30 ml), water (30 ml) and brine (30 ml). After drying over sodium sulfate the solvent was removed in vacuo and the residue subjected to silica gel column chromatography to afford the required amide 9.

General Procedure F

To a stirred solution of Boc-dolaproine 5 (1.74 mmol) in anhydrous dichloromethane (10 ml) cooled to -10° C., was added triethylamine (1.74 mmol, 1.0 equiv.) followed by isobutyl chloroformate (1.74 mmol, 1.0 equiv.) and the reaction was continued at -10° C. for 30 min. The amine (8a–g, 1.74 mmol, 1.0 equiv.) was added and

TABLE 2

Physical constants and spectroscopic data for the Boc-Dap-amino acid amides 6a–e

| no. | R | R$_7$ | yield % | mp ° C. | $[\alpha]_D^{25°}$, CHCl$_3$ | ir, $\nu_{max}$, cm$^{-1}$ | $^1$H nmr, δ | ms, M$^+$ |
|---|---|---|---|---|---|---|---|---|
| 6a | (CH$_2$)$_2$SMe | k | 88 | — | −44 (c 0.26) | 3277 1698 1676 1626 | 1.10(1H, m), 1.25(3H, dd), 1.30–1.53(7H, m), 1.48(9H, s), 1.65–2.10(9H, m), 2.12(3H, s), 2.26(1H, m), 2.32–3.0(5H, m), 3.27(1H, m), 3.43(3H, s), 3.46(1H, m), 3.81(2H, m), 4.06–4.32(2H, m), 4.50(1H, q), 6.6/6.9(1H, brs) | 551 |
| 6b | (CH$_2$)$_2$SMe | j | 36 | — | −93.5 (c 0.17) | 1695 1637 1545 | 0.79(3H, s), 0.82(3H, s), 1.09(3H, s), 1.24(5H, m), 1.43, 1.46, 1.49(9H, s), 1.34–1.60(2H, m), 1.67–2.02(8H, m), 2.10(3H, s), 2.40–2.65(3H, m), 3.20–3.27(2H, m), 3.44(3H, s), 3.55(1H, m), 3.83(2H, m), 3.92(1H, m), 4.49(1H, m), 6.50(1H, m), 6.7/7.1(1H, d) | 553 |
| 6c | (CH$_2$)$_2$SMe | n | 53 | — | −62 (c 1.18) | 2251 1684 1645 1537 | 1.27(3H, m), 1.32(9H, s), 1.47(1H, brm), 1.66–2.0(6H, m), 2.12(3H, s), 2.32(4H, m), 2.52(4H, m), 2.64(4H, t), 2.85(2H, m), 3.26/3.50(2H, m), 3.44(3H, s), 3.8(2H, m), 4.16(2H, t), 4.67(1H, m), 7.19(1H, d), 8.66/8.95(1H, s) | 576 |
| 6e | Ph | Ph | 21 | 204 | −119 (c 0.18) | 3306 3277 1698 1642 | 1.23(3H, d), 1.42(9H, s), 1.71(3H, m), 1.85(2H, m), 1.93(1H, m), 2.49(1H, t), 3.19(1H, m), 3.39(3H, s), 3.45, 3.83(1H, brs), 3.81(H, m), 5.61(1H, m), 7.08(1H, t), 7.25–7.36(6H, m), 7.44(3H, m), 7.80(1H, brs) | 463 (M$^+$- CH$_3$OH) |

Example 4

Deprotection of Boc-Dipeptide Amides 6a–e
General Procedure D

A solution of the Boc-dipeptide amide (6a–e, 0.1 mmol) in dry dichloromethane (2 ml)/trifluoroacetic acid (1 ml) was stirred at 0° C. for 2 lr under argon. The solvent was removed in vacuo and the residue dissolved in toluene and reconcentrated. The oily trifluoroacetate salts (7a–e) thus obtained were dried under high vacuum and used without further purification in the next coupling reaction. The general procedures of Examples 1–4 are depicted in Scheme I.

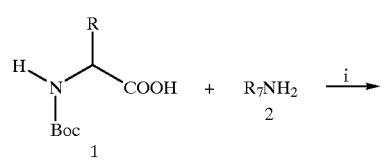

Scheme I

-continued d) R = -(CH₂)₂SMe, R₇ = [bicyclic structure]

e) R = phenyl, R₇ = phenyl i) ethyl chloroformate, triethylamine, dichloromethane
ii) trifluoroacetic acid, dichloromethane
iii) diethylphosphorocyanidate (DEPC), triethylamine, dichloromethane the reaction mixture stirred at −10° C. for 2 hr. The solvent was removed in vacuo, and the residue was dissolved in ethyl acetate. Triethylamine hydrochloride was collected by filtration and the filtrate was concentrated in vacuo. The residue was subjected to silica gel column chromatography to afford the required amides 9a–g.

Synthesis of N-tert-butoxycarbonyl-dolaproine 1-amino-bicyclo[3.3.0]octane Amide 9b Reaction of Boc-dolaproine (5) in anhydrous THF (20 ml) with 1-aminobicyclo[3.3.0]octane (8b) following General Procedure E gave a residue which was subjected to silica gel chromatography (eluent hexane-ethyl acetate; 4:1) to afford a colorless oil (9b, 64%); $[\alpha]_D^{25}=-40°$ (c 0.45, chloroform); IR(film): 3339, 2936, 1693, 1682, 1667, 1643 cm$^{-1}$; $^1$H NMR (300 MHz, CDCl₃) δ: 1.21(3H, d, J 5Hz), 1.23–1.29 (2H, m), 1.48(9H, s, Bu$^t$), 1.55–2.01(14H, m), 2.10–2.45 (2H, m), 3.26(1H, m), 3.33–3.65(1H, dm), 3.44(3H, s, OMe), 3.68–3.80(2H, dm), 5.68/6.39(1H, s, H); MS (m/z): 394(M$^+$, 0.1%), 362, 321, 262, 225, 210, 170, 154, 114 (100%), 70(100%) and 57.

TABLE 3

Physical constants and spectroscopic data for the Boc-Dap-amides 9a–g

| no. | R₇ | Yield % | mp °C. | $[\alpha]_D^{25°}$, CHCl₃ | ir, $v_{max}$, cm$^{-1}$ | $^1$H nmr, δ | ms, M$^+$ |
|---|---|---|---|---|---|---|---|
| 9a | o | 92 | — | −30 (c 0.72) | 3321 1815 1737 1693 1645 | 1.26(3H, d), 1.47(9H, s), 1.64(1H, m), 1.79(2H, m), 1.94(2H, m), 2.26–2.42(2H, m), 2.51(1H, m), 3.09(2H, m), 3.30(2H, m), 3.40(2H, m), 3.45(3H, s), 3.79(2H, d), 4.69(1H, m) | 372 |
| 9b | m | 27 | — | −18 (c 1.18) | 1691 1689 1662 | 1.26(3H, d), 1.47(9H, s), 1.53–2.05(6H, m), 2.50(1H, m), 2.88(1H, m), 3.21–3.41(4H, m), 3.45(3H, s), 3.83(1H, brd), 3.90(1H, m), 4.58(1H, m) | 354 |
| 9c | p | 63 | 174–180 | −49 (c 0.5) | 3227 1684 1642 | 1.29(3H, d), 1.45(9H, s), 1.72–2.04(4H, m), 2.62(1H, m), 2.89/2.97(1H, s), 3.25(1H, m), 3.48(4H, s), 3.94(2H, m), 7.98(1H, s), 8.32(2H, s) | 541 |
| 9e | j | 50 | — | −69 (c 1.02) | 3350 1694 1672 | 0.84(3H, s), 0.85(3H, s), 0.93(3H, m), 1.10–1.34(6H, m), 1.48(9H, s), 1.50–2.02(8H, m), 2.20–2.5(1H, m), 3.26(1H, m), 3.30–3.60(1H, m), 3.43(3H, s), 3.8(1H, brm), 3.86(2H, brm), 5.67/6.15(1H, brs) | 422 |
| 9f | k | 43 | — | −38 (c 0.44) | 3308 1694 1670 | 1.00–1.39(5H, m), 1.41–1,57(4H, m), 1.48(9H, s), 1.65–2.02(6H, m), 2.10(2H, m), 2.10–2.50(4H, m), 3.27(1H, m), 3.45(3H, s), 3.33– | 420 |

TABLE 3-continued

Physical constants and spectroscopic data for the Boc-Dap-amides 9a–g

| no. | R$_7$ | Yield % | mp °C. | $[\alpha]_D^{25°}$, CHCl$_3$ | ir, $v_{max}$, cm$^{-1}$ | $^1$H nmr, δ | ms, M$^+$ |
|---|---|---|---|---|---|---|---|
| | | | | | 1643 | 3.63(1H, brd), 3.70–3.90(2H, brm), 5.67/6.15(1H, brs) | |
| 9g | r | 57 | — | -30 (c 0.66) | 1668 1665 | 1.33(3H, m), 1.48(9H, s), 1.65(4H, m), 1.79(1H, m), 1.94(4H, d), 2.24(1H, m), 2.65(1H, m), 2.80(2H, t), 3.27(1H, m), 3.39–3.60(1H, m), 3.50(3H, s), 3.92(2H, m), 4.34(2H, d), 6.67(1H, d), 7.6–8.37(3H, m) | 514 |

Example 6

Deprotection of the Boc-Dolaproine Amides 9a–g
General Procedure G

A solution of the Boc-dolaproine amide (9a–g, 0.1 mmol) in dry dichloromethane (2 ml)-trifluoroacetic acid (1.0 ml) was stirred at 0° C. for 2 hr under argon. The solvent was removed in vacuo and the residue taken up in toluene and reconcentrated. The oily trifluoroacetate salts (10a–g) obtained were dried under high vacuum and used without further purification in the next coupling reaction. The general procedures of Examples 5 and 6 are depicted in Scheme II.

Example 7

Synthesis of the Pentapeptide Amides 12a–e
General Procedure H

To a solution of the above trifluoroacetate salt of the dipeptide amide (7a–e, 0.1 mmol) or the trifluoroacetate salt of the dolaproine amide (10a–g, 0.1 mmol) and the tripeptide trifluoroacetate salt (Tfa*Dov-Val-Dil-COOH, 11, 0.1 mM) in dry dichloromethane (2 ml) cooled to ice-bath temperature under argon was added triethylamine (3–4 eq.) followed by DEPC (1.2 eq.) and the solution was stirred at the same temperature for 2 hr. The solvent was removed in vacuo and the residue chromatographed on a silica gel column to provide the respective pentapeptide amides (12a–e) or the tetrapeptide amides (13a–g). This procedure is depicted in Scheme II.

Synthesis of Dov-Val-Dil-Dap-Met 1-(bicyclo [3.3.0]octane) Amide (12d)

Reaction of the trifluoroacetate 7d with tripeptide trifluoroacetate 11 following General Procedure G gave, following chromatography (silica gel column using 3:1 acetone-hexane as eluent), the required pentapeptide amide as a colorless glassy solid (12d, 94%); R$_f$=0.55 (dichloromethane-methanol 8:1); $[\alpha]_D^{25}$=-36.5° (c 0.17, chloroform); mP 95–102 ° C.; IR(thin film): 3574, 3509, 3493, 3476, 3293, 3059, 2959, 2936, 2878, 2832, 1643, 1622, 1547, 1539, 1504, 1445, 1416, 1385, 1371, 1337, 1283, 1271, 1223, 1198, 1167, 1036 cm$^{-1}$; $^1$H NMR(300 MHz, CDCl$_3$, partial assignment): 6.98(d), 6.9(d), 6.56(s), 4.76(m), 4.40(q), 4.26(m), 4.09(m), 3.92(dd), 3.38(s), 3.30 (s), 3.00(s) and 2.09(s); MS {m/z(%)}: 836(M$^+$), 793, 763, 684, 611, 481, 412, 227, 186(100) and 170; Anal. Found: C, 61.97, H, 9.34, N, 9.71; C$_{44}$H$_{80}$N$_6$O$_7$S.H$_2$O requires: C, 61.79, H, 9.66, N, 9.83%.

TABLE 4

Physical constants and spectroscopic data for the pentapeptide amides 12a–e

| no. | R | R$_7$ | yield % | mp °C. | R$_f$ | $[\alpha]_D^{25}$ °CHCl$_3$ | ir, $v_{max}$, cm$^{-1}$ | $^1$H nmr, δ | ms M$^+$ | Molecular Formula |
|---|---|---|---|---|---|---|---|---|---|---|
| 12a | (CH$_2$)$_2$SMe | k | 77 | 114–120 | 0.46 (3:2 acetone-hexane) | -54 (c 0.19) | 3293 1641 1626 | 6.99(d), 4.76(t), 4.45(m), 4.1(m), 3.31(s), 3.3(s), 3.25(s), 3.0(s), 2.99(s), 2.27(s), 2.1(s), 2.09(s) | 862 | C$_{46}$H$_{82}$N$_6$O$_7$S. 3H$_2$O |
| 12b | (CH$_2$)$_2$SMe | j | 84 | 98–103 | 0.54 (3:2 acetone-hexane) | -83 (c 0.06) | 3293 1647 1624 | 7.21(d), 6.53(d), 4.75(t), 4.43(q), 4.19(m), 4.09(m), 3.38(s), 3.29(s), 3.0(s), 2.09(s) | 864 | C$_{46}$H$_{84}$N$_6$O$_7$S. 3H$_2$O |
| 12c | (CH$_2$)$_2$SMe | n | 96 | — | 0.48 (8:1 dichloro-methane methanol) | -34.5 (c 0.29) | 3395 2280 1643 1624 | 7.49(d), 4.7(m), 4.23(m), 3.92(m), 3.41(s), 3.28(s), 2.96(s), 2.46(bs), 2.13(s), 1.36(t) | 887 | C$_{45}$H$_{78}$N$_9$O$_9$S |
| 12e | Ph | Ph | 94 | — | — | -87.5 (c 0.12) | 3290 1643 1622 | 7.54(m), 7.46(m), 7.31(m), 7.07(m), 6.92(d), 5.2–6.4(d), 4.75(m), 4.12(m), 3.87, 3.98(m), 3.73(m), 3.56(dd), 3.28(m), 3.32(s), 3.37, 3.39(s), 3.20(d), 2.99, 3.11(s) | 806 | C$_{45}$H$_{70}$N$_6$O$_7$. H$_2$O |

Scheme II

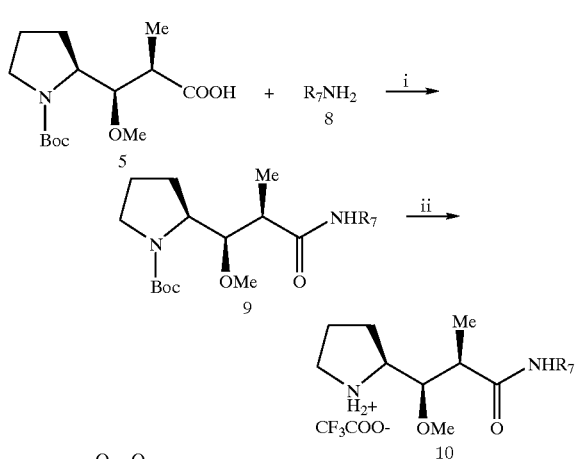

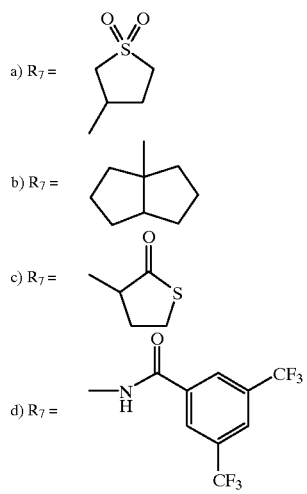

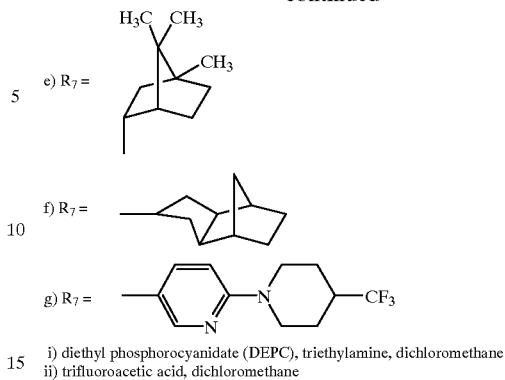

i) diethyl phosphorocyanidate (DEPC), triethylamine, dichloromethane
ii) trifluoroacetic acid, dichloromethane

Example 8

Synthesis of the Tetrapeptide Amides 13a–g

Dov-Val-Dil-Dap 1-bicyclo[3.3.0]octane amide (13b)

Coupling the trifluoroacetate 10b with the tripeptide trifluoroacetate 11 according to General Procedure H, followed by chromatography (silica gel column) of the residue in 2:1 acetone-hexane, gave the required tetrapeptide amide (13b, 89%) as a colorless glassy solid; $R_f$=0.61 (3:2 acetone-hexane); $[\alpha]_D^{25}$=−44° (c 0.17, CHCl$_3$); mP 97–102° C.; IR(thin film): 3308, 2959, 2936, 2872, 2830, 1622, 1534, 1489, 1451, 1418, 1385, 1371, 1339, 1267, 1217, 1200, 1132, 1099 and 1038 cm$^{-1}$; $^1$H NMR(300 MHz, CDCl$_3$, partial assignment): 6.92(m), 6.31(s), 4.86(m), 4.76(q), 4.04–4.15(m), 3.38(s), 3.32(s), 3.30(s), 3.08(s), 2.99(s), 2.28–2.40(m), 1.56(pentet); MS(m/z): 705(M$^+$), 662, 525, 481, 449, 379, 293, 227, 199, 186 and 155(100%). This procedure is depicted in Scheme IV.

TABLE 5

Physical constants and spectroscopic data for the tetrapeptide amides 13a–g

| no. | R$_7$ | yield % | mp ° C. | R$_f$ | $[\alpha]_D^{25}$ °CHCl$_3$ | ir, $^\nu$max, cm$^{-1}$ | $^1$H nmr, δ | ms M$^+$ | Molecular Formula |
|---|---|---|---|---|---|---|---|---|---|
| 13a | o | 62 | 85–90 | 0.29 (3:2 acetone-hexane) | −22 (c 0.14) | 3291 1670 1647 | 7.79(d), 4.63–4.8(m), 4.0(m), 3.85(m), 3.39/3.38(s), 3.34/3.31/3.3(s), 2.99(s), 2.83(bs) | 715 | C$_{35}$H$_{65}$N$_5$O$_8$S |
| 13c | p | 70 | 90–98 | 0.46 (3:2 acetone-hexane) | −93 (c 0.06) | 3293 1701 1624 | 7.15(d), 4.76(m), 4.6(m), 4.23(m), 4.07(m), 3.87(dd), 3.71(t), 3.39/3.32/3.31(s), 2.98(s), 2.34(s), 1.26(d) | 697 | C$_{35}$H$_{63}$N$_5$O$_7$S.3 H$_2$O |
| 13d | q | 45 | 115–122 | 0.56 (3:2 acetone-hexane) | −45 (c 0.1) | 3256 1672 1626 | 8.33(s), 7.94(s), 4.63(s), 3.96(s), 3.43/3.41(s), 3.39(s)/3.31(s), 3.03(s) | 852 | C$_{40}$H$_{62}$N$_6$O$_7$F$_6$.4 H$_2$O |
| 13e | j | 34 | — | 0.25 (1:1 acetone-hexane) | −37 (c 0.26) | 1622 | 4.79, 4.87(q), 4.12(m), 3.92(dd), 3.4/3.41(s), 3.31/3.33(s) | 733 | C$_{41}$H$_{75}$N$_5$O$_6$.H$_2$O |
| 13f | k | 97 | 75–80 | 0.35 (1:1 acetone-hexane) | −21 (c 2.7) | 1640 | 7.25(d), 4.68–4.77(m), 4.25(m), 4.10(m), 3.86(d), 3.40/3.32(s), 3.01(s), 1.25(d) | 731 | C$_{41}$H$_{73}$N$_5$O$_6$ |
| 13g | r | 50 | 83–88 | 0.52 (2:3 acetone-hexane) | −37 (c 2.1) | 1669 1632 | 8.54(s), 8.27(d), 7.95(dd), 6.92(m), 6.65(m), 4.77(m), 4.01(d), 3.46(s), 3.34(s), 3.02(s) | 825 | C$_{42}$H$_{70}$N$_7$O$_6$F$_3$ |

Scheme III

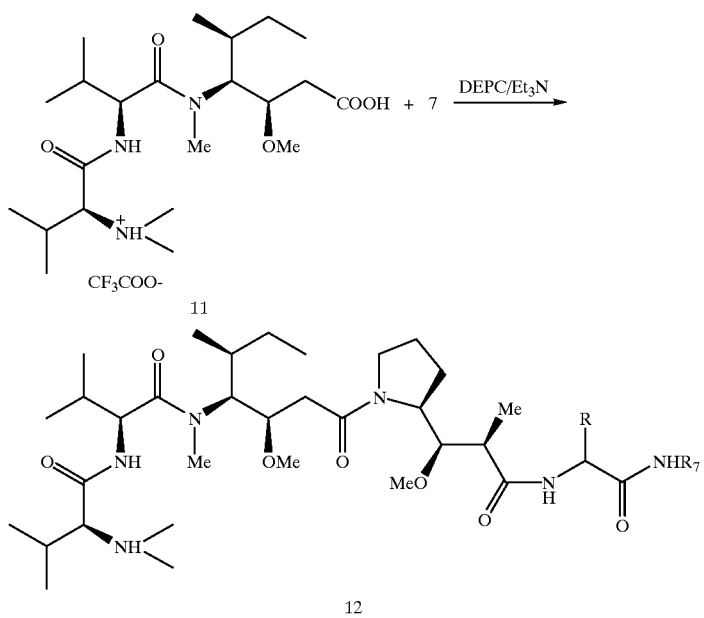

Scheme IV

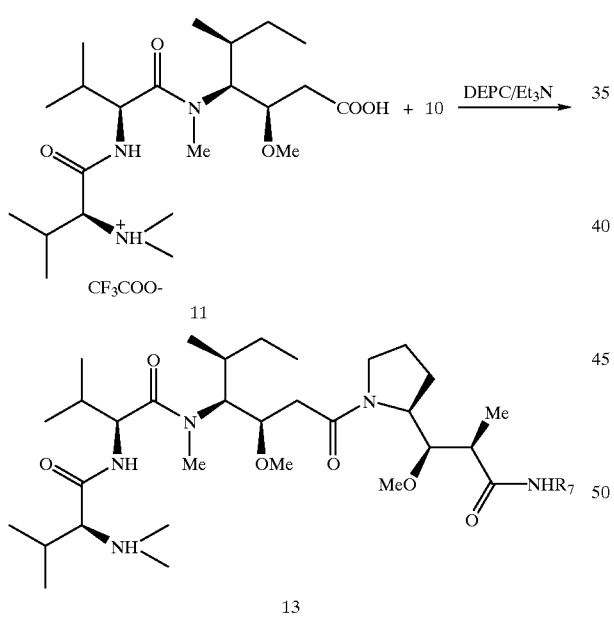

Example 9

Synthesis of N-t-Boc Amino Acid Amides 16a–g

Synthesis of t-Boc-phenylalanine Amide 16d

A solution of N-t-Boc-Phenylalanine (1 g, 3.77 mM) in anhydrous tetrahydrofuran (25 ml) was cooled to −15° C. and neutralized with N-methylmorpholine (450 μl). Isobutyl chloroformate (550 μl) was added followed by 3-amino-(5-thiomethyl)thia-1,4-diazole (2i, 550 mg, 3.77 mM). The reaction mixture was allowed to warm to room temperature. After stirring for 1 h, the inorganic salts were collected and the organic layer was concentrated and chromatographed on a silica gel column using 2:1 hexane-acetone as eluent to yield the required amide as a colorless solid (16d, 0.82 g, 55%): $R_f$=0.6 (3:2 hexane-ethyl acetate); $[\alpha]_D^{25}$=−44° (c 0.12, chloroform); mP 56–60° C.; IR(neat): 3271, 3194, 2976, 2928, 1682, 1537, 1437, 1392, 1368, 1285, 1231, 1163, 1049, 1024 cm$^{-1}$; $^1$H NMR (300 MHz, CDCl$_3$): 5.25(m, 1H, NH), 4.60(m, 1H, C$^\alpha$—H), 2.83(s, 3H, ArS—Me), 2.82(t, 2H, S—CH$_2$), 2.15–2.30(m, 1H, ½CH$_2$), 2.09(s, 3H, ArS—Me), 1.95–2.05(m, 1H, ½CH$_2$), 1.65(s, 1H, NH), 1.44(s, 9H, t-Bu); MS(m/z): 378(M$^+$), 304, 278, 204, 174, 131, 104 and 57(100%).

Synthesis of the other amides 16a–c, e–g were all carried out in the same manner as described above.

TABLE 6

Physical and spectroscopic data for the t-Boc-amino acid amides 16a–g.

| no. | n | R | Ar | yield % | mp ° C. | $R_f$ | $[\alpha]_D^{25}$ CHCl$_3$ | ir, $\nu$max, cm$^{-1}$ | $^1$H nmr, δ | ms M$^+$ |
|---|---|---|---|---|---|---|---|---|---|---|
| 16a | 1 | (CH$_2$)$_2$SMe | s | 83 | 174–175 | 0.37 (3:2 hexane-ethyl-acetate) | −91 (c 0.2) | 3308(br) 1717(br) | 7.45(d, NH), 4.62(m, C$^\alpha$—H), 2.70(t, S—CH$_2$), 2.04(s, 3H, S—Me) | 408 |

TABLE 6-continued

Physical and spectroscopic data for the t-Boc-amino acid amides 16a–g.

| no. | n | R | Ar | yield % | mp °C. | $R_f$ | $[\alpha]_D^{25}$ CHCl$_3$ | ir, $\nu$max, cm$^{-1}$ | $^1$H nmr, $\delta$ | ms M$^+$ |
|---|---|---|---|---|---|---|---|---|---|---|
| 16b | 1 | (CH$_2$)$_2$SMe | t | 12 | — | 0.52 (3:2 hexane-ethyl-acetate) | −40 (c 0.12) | 3217(br) 1682(br) | 5.25(m, NH), 4.60(m, C$^\alpha$—H), 2.83(s, S—CH$_2$), 2.82(t, S—CH$_2$), 2.09(s, S—Me) | 378 |
| 16c | 1 | (CH$_2$)$_2$SMe | u | 52 | 146–149 | 0.43 (7:3 hexane-acetone) | −51 (c 0.16, MeOH) | 3217(br) 1713, 1688 | 5.25(m, NH), 4.50(m, C$^\alpha$—H), 2.86(t), 2.74(t), 2.56(t), 2.07(s), 1.43(s) | 371 |
| 16e | 1 | CH$_2$Ph | t | 88 | 196–198 | 0.45 (3:2 hexane-ethyl-acetate) | −62 (c 0.38) | 3297(br) 1715(br) | 7.10(m, NH), 4.80(m, C$^\alpha$—H), 3.30(dd, 1H), 3.05(dd, 1H), 1.19(s, Bu$^t$) | 424 |
| 16f | 2 | (CH$_2$)$_2$SMe | v | 76 | 98–99 | 0.17 (3:1 hexane-acetone) | −45.5 (c 1.0) | 3297(br) 1667(br) | 7.40(d), 7.06(d), 4.44(m), 3.87(s), 2.09(s), 1.40(s) | 660 |
| 16g | 2 | (CH$_2$)$_2$SMe | w | 52 | — | 0.19 (3:1 hexane-acetone) | −7.4 (c 0.38) | 3308(br) 1692(br) | 7.72(d), 7.58(dd) 4.46(m), 2.09(s), 1.41(s), 0.90(d) | 571 |

Example 10

Synthesis of the Dipeptide Amides 19a–g

Synthesis of Boc-Dap-Phe Amide 19d

A solution of t-Boc-phenylalanine amide (100 mg, 0.25 mM) in dry dichloromethane (2 ml) trifluoroacetic acid (2 ml) was stirred at 0° C. for 2 hr under argon. The solvent was removed in vacuo and the reside dissolved in toluene and reconcentrated twice. The oily trifluoroacetate salt 17d was dried under high vacuum.

To a solution of the above trifluoroacetate salt and t-Boc-dolaproine (5, 75 mg, 0.26 mM) in dry dichloromethane (3 ml) cooled to 0° C., was added triethylamine (145 μl, 4 eq.) followed by diethyl phosphorocyanidate (DEPC, 50 μl, 1.2 eq.). The mixture was stirred for 2 hr at 0° C. The solvent was removed in vacuo and the residue was chromatographed on a silica gel column with 2:1 hexane-acetone as the eluent to afford the required dipeptide amide as a colorless solid (19d, 93 mg, 69%); mP 49–52° C.; $R_f$=0.28 (1:2 acetone-hexane); $[\alpha]_D^{25}$=−72.7° (c 0.11, chloroform); IR(thin film): 3306, 3292, 3277, 3190, 3179, 3061, 3032, 2976, 2932, 2880, 1690, 1656, 1651, 1547, 1501, 1478, 1454, 1402, 1368, 1321, 1229, 1169, 1115, 1065 and 1034cm$^{-1}$; $^1$HNMR (300 MHz, CDCl$_3$): 7.21–7.32(m, 5H, Ph), 6.95(brd, 1H, NH), 4.84(m, 1H, C$^\alpha$—H), 4.20(m, 1H, C$^\alpha$—H), 3.37(s, 3H, O—Me), 2.60(s, 3H, S—Me), 1.45(s, 9H, But), 1.05(d, J 7. Hz, 3H, CH$_3$); MS(m/z): 531(M$^+$), 505, 490, 431, 394, 379, 350, 210, 170 and 114(100%).

The general procedures of Examples 9 and 10 are depicted in Scheme V.

TABLE 7

Physical and spectroscopic data for the t-Boc-Dap-amino acid amides 19a–g.

| no. | n | R | Ar | yield % | mp °C. | $R_f$ | $[\alpha]_D^{25}$ Chloroform | ir, $\nu$max, cm$^{-1}$ | $^1$H nmr, $\delta$ | ms, M$^+$ |
|---|---|---|---|---|---|---|---|---|---|---|
| 19a | 1 | (CH$_2$)$_2$SMe | s | 69 | 49–52 | 0.28 (1:2 acetone-hexane) | −72.7 (c 0.11) | 3306(br) 1690, 1656, 1651 | 7.38(d), 4.75(m), 4.28(m), 3.45(s), 2.59(s), 2.12(s), 1.45(s) | 557 |
| 19b | 1 | (CH$_2$)$_2$SMe | t | 81 | — | 0.3 (1:2 acetone-hexane) | −48.2 (c 0.11) | 3325(br) 1692, 1597, 1582 | 4.83(m), 3.88(m), 3,78(s), 2.71(s), 2.07(s), 1.45(s) | 577 |
| 19c | 1 | (CH$_2$)$_2$SMe | u | 56 | 164–167 | 0.4 (3:7 acetone-hexane) | −69.3 (c 0.43, MeOH) | 3190, 1692, 1651 | 7.36(bs), 6.86(bs), 4.84(m), 3.40(s), 1.98(s), 1.43(s) | 540 |
| 19e | 1 | CH$_2$Ph | t | 74 | 79–82 | 0.32 (1:2 acetone-hexane) | −43.8 (c 0.21) | 3295(br) 1692(br) | 7.86(d), 7.49(m), 7.27(s), 5.05(s), 3.25(s), 1.46(s) | 593 |
| 19f | 2 | (CH$_2$)$_2$SMe | v | 20 | 207–209 | 0.73 (8:1 dichloromethane-methanol) | −120 (c 0.02) | 3289(br) 1692, 1636, 1607 | 7.51(d), 7.05(m), 4.65(m), 3.41(s), 2.11(s), 1.41(s) | 579 (M$^+$ -419) |
| 19g | 2 | (CH$_2$)$_2$SMe | w | 40 | 65–69 | 0.07 (1:3 acetone-hexane) | −53.5 (c 0.17) | 3306(br) 1692, 1667 | 7.57–7.65(b), 7.76(d), 4.67(m), 3.42(s), 2.01(s) 1.43(s) | 909 |

Scheme V

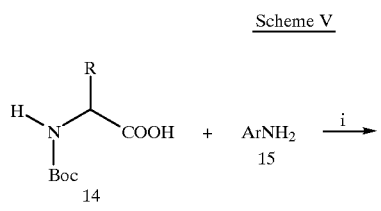

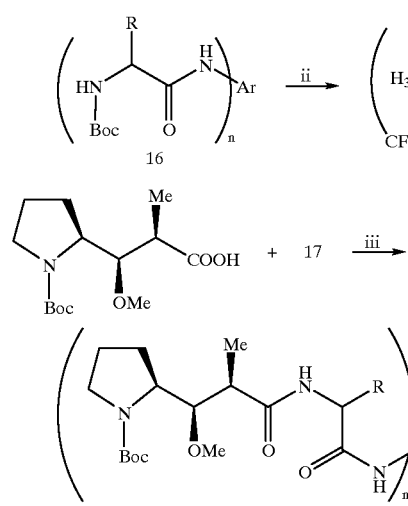

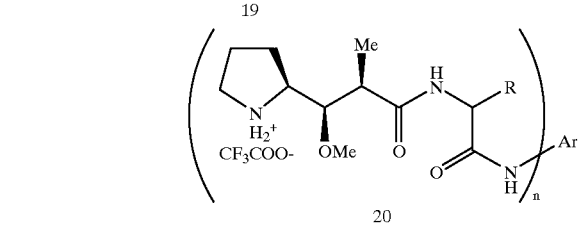

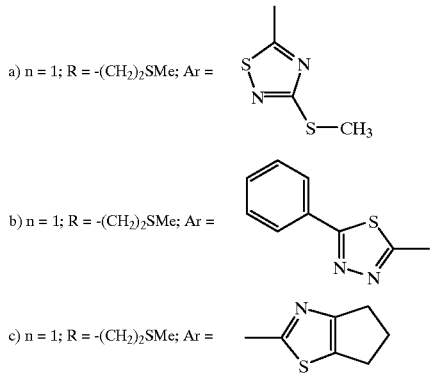

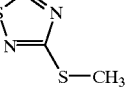

d) n = 1; R = -CH₂Ph; Ar =

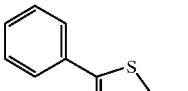

e) n = 1; R = -CH₂Ph; Ar =

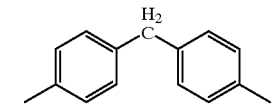

f) n = 2; R = -(CH₂)₂SMe; Ar =

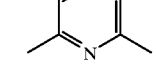

g) n = 2; R = -(CH₂)₂SMe; Ar = i) ethyl chloroformate, triethylamine, dichloromethane
ii) trifluoroacetic acid, dichloromethane
iii) diethylphosphorocyanidate (DEPC), triethylamine, dichloromethane

Example 11

Synthesis of N-Boc-dolaproine Amides 22a–h

N-t-Boc-Dolaproine-2-(p-aminophenyl)ethylamide 22d

To a solution of Boc-dolaproine (0.3 g, 1.05 mmole) and p-amino-phenethylamine (0.15 ml, 1.1 eq) in dry dichloromethane (15 ml) at 0° C. under nitrogen was added triethylamine (0.44 ml, 3 eq.) followed by diethyl phosphorocyanidate (0.22 ml, 1.4 eq.). After stirring for 1 hr, the solvent was removed in vacuo. The residue was purified by flash chromatography on a silica gel column using 3:7 acetone-hexane to get the required amide as a clear liquid (22d, 0.56 g, 100%); $R_f$=0.34 (1:1 acetone-hexane); $[\alpha]_D^{25}$=−43° (c 0.34, MeOH); IR(neat): 3341, 2972, 2934, 2876, 1667, 1547, 1518, 1454, 1406, 1366, 1256, 1169, 1107 cm⁻¹; ¹H NMR(300 MHz, CDCl₃): 6.97(bs), 6.61(d), 3.52 (t), 3.47(t), 3.37(s), 1.56(m), 1.47(bd), 1.36(m); MS(m/z): 405(M⁺), 373, 332, 287, 261, 255, 221, 187, 170, 159, 138, 119(100%).

This general procedure is depicted in Scheme VI.

TABLE 8

Physical and spectroscopic data for the t-Boc-Dap-amides 22a–h.

| no. | n | R₆ | R₇ | yield % | mp ° C. | $R_f$ | $[\alpha]_D^{25}$ °Chloroform | ir, $\nu$max, cm⁻¹ | ¹H nmr, δ | ms M⁺ |
|---|---|---|---|---|---|---|---|---|---|---|
| 22a | 1 | H | a | 82 | — | 0.45 (5:1 dichloromethane-methanol) | −50.8 (c 0.13) | 3497 (br) 1692 1643 | 3.42 (s, OMe), 1.18 (d, 6.6 Hz, Me) | 437 |
| 22b | 1 | H | b | 64 | — | 0.33 (1:1 acetone-hexane) | −35.0 (c 0.14, Methanol) | 3351 (br) 1690, 1528 | 10.06 (NH), 8.80 (d), 8.76 (d), 8.14 (d), 7.49 (t), 7.42 (t), 3.51 (s), 1.45 (s) | 413 |

TABLE 8-continued

Physical and spectroscopic data for the t-Boc-Dap-amides 22a–h.

| no. | n | $R_6$ | $R_7$ | yield % | mp °C. | $R_f$ | $[\alpha]_D^{25}$ °Chloroform | ir, $\nu$max, cm$^{-1}$ | $^1$H nmr, $\delta$ | ms M$^+$ |
|---|---|---|---|---|---|---|---|---|---|---|
| 22c | 1 | H | d | 81 | — | 0.44 (1:1 acetone-hexane) | −50.3 (c 0.3, Methanol) | 3157 (br) 1694 1549 | 3.49 (s), 2.96 (m), 2.29 (m), 1.44 (s), 1.33 (d) | 410 |
| 22e | 1 | H | g | 17 | — | 0.48 (1:1 acetone-hexane) | −31.0 (c 0.21, Methanol) | 3319 1688 1516 | 6.96 (d), 6.63 (d), 4.78 (m), 4.19 (t), 3.50 (s), 1.46 (s) | 405 M$^+$ -FMOC |
| 22f | 1 | i | COOMe | 88 | — | 0.75 (1:1 acetone-hexane) | −17.6 (c 0.37, Methanol) | 3308 1670 1543 | 7.95 (m), 7.24 (m), 6.85 (d), 3,86 (s), 3.35 (s), 1.80 (m), 1.47 (s), 1.19 (d) | 459 |
| 22g | 1 | −CH$_2$Ph | c | 84 | 104–106 | 0.25 (2:1 hexane-acetone) | −6.3 (c 0.16) | 3308 (br) 1746 1686 | 8.73 (d), 7.05 (m), 6.83 (m), 4.89 (m), 3.69 (s), 3.38 (s), 1.47 (s), 1.19 (d) | 455 |
| 22h | 2 | NR$_6$R$_7$= | f | 82 | — | 0.29 (3:2 hexane-acetone) | −53.2 (c 0.22) | 1692 1645 | 3.42 (s, O—Me), 1.2 (d, 6.8 Hz, Me), 1.47 (s) | 624 |

Scheme VI

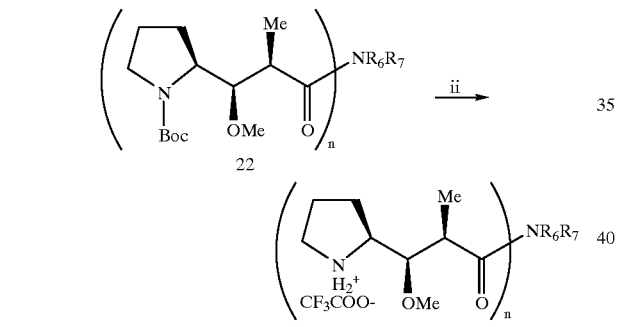

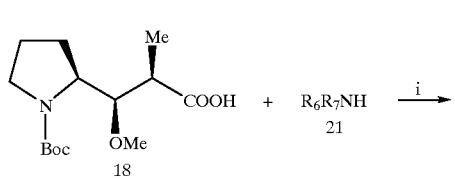

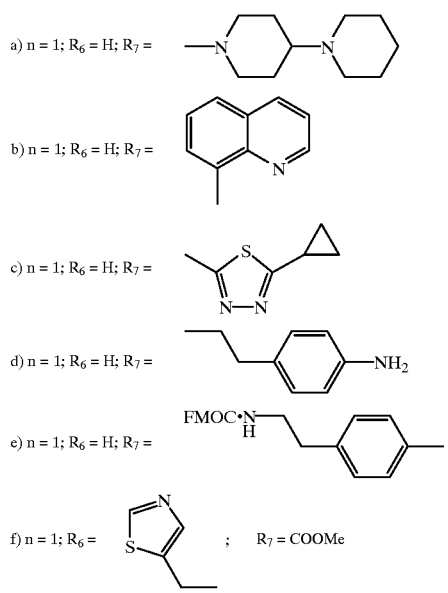

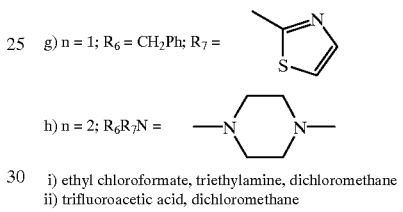

i) ethyl chloroformate, triethylamine, dichloromethane
ii) trifluoroacetic acid, dichloromethane Example 12

Synthesis of Tripeptides (26a–e)

Synthesis of Diethyl Val-Leu-Dil-COOBu$^t$ 26b

N-Z-(S)-Leu-Dil-OBu$^t$ (24b, 0.12 g, 0.237 mM) was dissolved in anhydrous methanol (5 ml) under nitrogen. Cyclohexene (5 ml) was added followed by Pd-C (5%, 0.12 g) and the solvent was immediately heated to reflux. The solution was maintained at reflux for 6 min, cooled, filtered through celite and concentrated to a clear oil which was dried under vacuum for 2 h.

N,N-diethyl-valine (25b, 0.05 g, 0.285 mmol) was dissolved in dry dichloromethane (5 ml) under nitrogen. The solution was cooled to 0° C. and triethylamine (0.04 ml, 0.284 mM) was added followed by DEPC (0.04 ml, 0.28 mM). The dipeptide was added to this mixture, the solution was allowed to warm to ambient temperature, and stirred for 1 h. The mixture was concentrated under reduced pressure and chromatographed over silica gel (3:17 acetone-hexane) to give the tripeptide as a clear liquid (24b, 0.129 g, 96%); R$_f$=0.73(1:3 acetone-hexane); $[\alpha]_D^{25}$=−47.8° (c 0.13, MeOH); IR(neat): 3308, 2965, 1730, 1628, 1524, 1468, 1290, 1155, 1103 cm$^{-1}$; $^1$H NMR (300 MHz, CDCl$_3$): 6.69(bd), 4.97(m), 3.85(m), 3.31(s), 1.43(s), 0.96(t); MS(m/z): 527(M$^+$), 485, 457, 270, 242, 186, 128(100%) and 100.

This procedure is depicted in Scheme VII.

TABLE 9

Physical and spectroscopic data for tripeptide 26c

| $R_4$ | $R_3$ | $R_1, R_2$ | yield % | $R_f$ | $[\alpha]_D^{25}$ ° | ir, $\nu$max, cm$^{-1}$ | $^1$H nmr, δ | ms, M$^+$ |
|---|---|---|---|---|---|---|---|---|
| Bu$^i$ | Bu$^s$ | Me | 64 | 0.51 (1:3 acetone-hexane) | −29.3 (c 0.8, methanol) | 3308 (br) 1730, 1628 | 6.89 (bd), 4.96 (m), 3.86 (m), 3.32 (s), 1.44 (s) | 513 |

Scheme VII

24

26

27 a) $R_4$ = Pr$^i$; $R_3$ = Pr$^i$; $R_1$ = $R_2$ = Me
b) $R_4$ = Bu$^i$; $R_3$ = Pr$^i$; $R_1$ = $R_2$ = Et
c) $R_4$ = Bu$^i$; $R_3$ = Bu$^s$; $R_1$ = $R_2$ = Me
i) H$_2$/Pd-C, cyclohexene, methanol
ii) DEPC, triethylamine, dichloromethane;

25 iii) trifluoroacetic acid, dichloromethane

Example 13

Synthesis of Pentapeptide Amides 28a–g

Synthesis of Dov-Val-Dil-Dap-Phe Amide 28d

To a solution of the dipeptide amide (20d, 30 mg, 0.057 mM) in dichloromethane (1 ml) cooled to 0° C. under argon was added trifluoroacetic acid (1 ml). The solution was stirred at the same temperature for 2 hr. Solvent was removed in vacuo and the residue was dissolved in toluene and reconcentrated twice. The oily trifluoroacetate salt was dried in vacuo.

To a solution of the above salt and the tripeptide trifluoroacetate salt (Tfa*Dov-Val-Dil-COOH, 27a, 31 mg, 0.057 mM) in dry dichloromethane (2 ml) cooled to 0° C. (under argon) was added triethylamine (32 μl, 4 eq) followed by DEPC (11.5 μl, 1.2 eq.). The solution was stirred at the same temperature for 2 hr. Solvent was removed ill vacuo and the residue was chromatographed on a silica gel column using 2:1 acetone-hexane as the solvent: $[\alpha]_D^{25}$=−50° (c 0.1, chloroform); mP 88–92° C.; IR(thin film): 3291, 2963, 2932, 2876, 2832, 1622, 1549, 1499, 1452, 1416, 1387, 1267, 1229, 1200, 1171, 1099 and 1038 cm$^{-1}$; $^1$H NMR(300 MHz, CDCl$_3$): 7.20–7.30(m, Ph), 5.04–5.10(m), 4.75–4.87(m), 4.57(m), 3.38(s), 3.35(s), 3.33(s), 3.31(s), 3.14(s), 3.07(s), 2.61(s); MS(m/z): 874(M$^+$).

This procedure is depicted in Scheme VIII.

TABLE 10

Physical and spectroscopic data for the dolastatin analogs 28a–g

| no. | n | R | Ar | yield % | mp ° C. | $R_f$ | $[\alpha]_D^{25}$ °Chloroform | ir, $\nu$max, cm$^{-1}$ | $^1$H nmr, δ | ms, M$^+$ | Molecular Formula |
|---|---|---|---|---|---|---|---|---|---|---|---|
| 28a | 1 | (CH$_2$)$_2$SMe | s | 48 | 110–116 | 0.5 (3:2 acet/hex) | −34.7 (c 0.32) | 3275 1643 1620 | 4.80, 3.44, 3.32, 2.59, 2.12 | 858 | C$_{39}$H$_{70}$N$_8$O$_7$S$_3$ |
| 28b | 1 | (CH$_2$)$_2$SMe | t | 36 | 130–135 | 0.36 (3:2 acet/hex) | −51 (c 0.1) | 3293 1622 | 7.87–7.93, 7.44, 3.44, 3.37, 3.34, 3.29, 3.09, 3.04, 2.13, 2.10 | 888 | C$_{44}$H$_{72}$N$_8$O$_7$S$_2$.2.5H$_2$O |
| 28c | 1 | (CH$_2$)$_2$SMe | u | 65 | 79–83 | 0.20 (1:1 acet/hex) | −65 (c 0.18, | 3271 1649 | 4.78, 3.50, 3.36, 3.32, | 851 | C$_{42}$H$_{73}$N$_7$O$_7$S$_2$ |

TABLE 10-continued
Physical and spectroscopic data for the dolastatin analogs 28a–g
| no. | n | R | Ar | yield % | mp ° C. | $R_f$ | $[\alpha]_D^{25}$ °Chloroform | ir, $\nu_{max}$, cm$^{-1}$ | $^1$H nmr, δ | ms, M$^+$ | Molecular Formula |
|---|---|---|---|---|---|---|---|---|---|---|---|
| | | | | | | methanol) | | 1622 | 3.28, 3.11, 3.04, 2.07 | | |
| 29e | 1 | CH$_2$Ph | t | 75 | 123–126 | 0.33 (2:1 acet/hex) | −52.9 (c 0.14) | 3291 1622 | 7.86–7.93, 7.45, 7.26 3.35, 3.32, 3.31, 3.11, 3.03 | 904 | C$_{48}$H$_{72}$N$_8$ O$_7$S$_2$ |
| 28f | 2 | (CH$_2$)$_2$SMe | v | 62 | 107–115 | 0.45 (8:1 dichloromethane-methanol) | −47.5 (c 0.08) | 3385 1643 1624 | 7.37, 7.04, 3.39, 3.28, 2.94, 2.10, 2.23 | 1620 | C$_{85}$H$_{144}$N$_{12}$ O$_{14}$S$_2$ |
| 28g | 2 | (CH$_2$)$_2$SMe | w | 17 | 106–110 | 0.28 (2:1 acet/hex) | −55.0 (c 0.06) | 3291 1642 1626 | 3.38, 3.35, 3.33, 2.99, 2.23, 2.10 | 1533 (M + H)$^+$ | C$_{77}$H$_{137}$N$_{13}$ O$_{14}$S$_2$ |
Scheme VIII
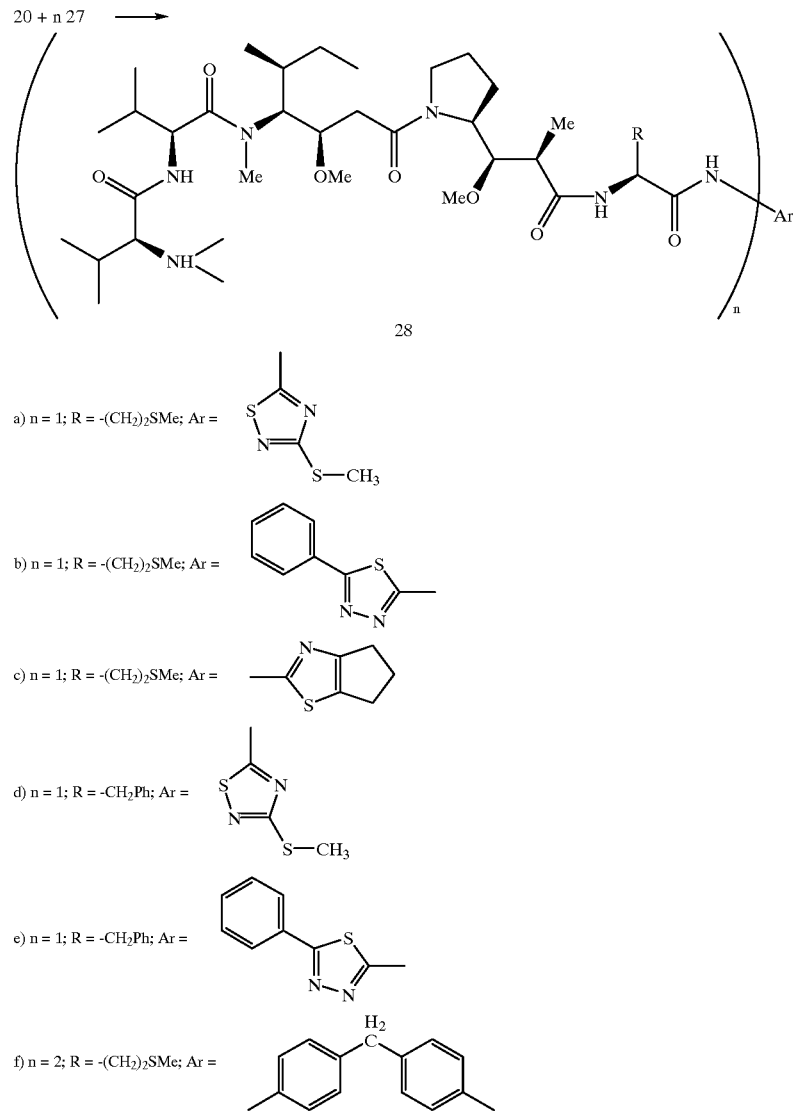

g) n = 2; R = -(CH₂)₂SMe; Ar = 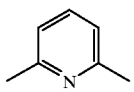

i) diethylphosphorocyanidate (DEPC), triethylamine, dichloromethane

Example 14

Synthesis of Tetrapeptide Amides 29a–l

Synthesis of Dov-Val-Dil-Dap 2-[p-aminophenyl]ethylamide 29d

A solution of the dipeptide Boc-Dap-2-p-aminophenylethylamide (22d, 0.56 g, 1.38 mM) in dichloromethane (35ml) was cooled to 0° C. (under nitrogen). Triethylamine (0.4 ml, 2.1 eq) was added followed by Fmoc-Cl (0.75 g, 2.1 eq) and the solution was stirred at room temperature for 30 min. Solvent was removed under reduced pressure and the residue chromatographed on a silica gel column using acetone-hexane (1:9 to 1:1 gradient) as the solvent to afford the required Fmoc protected peptide (0.43 g, 50%).

A solution of the above compound (0.38 g, 0.61 mM) in dichloromethane (0.5 ml) was cooled to 0° C. under nitrogen and trifluoromethane (0.5 ml) was added. The solution was stirred at the same temperature for 1 hr. The solvent was removed and the residue dried in vacuo. To a solution of the trifluoroacetate salt and the tripeptide trifluoroacetate salt (27a, 0.38 g, 0.61 mM) in dry dichloromethane (5 ml), cooled to 0° C. under nitrogen, was added DEPC (0.14 ml, 1.5 eq) followed by triethylamine (0.42 ml, 5.0 eq). The solution was stirred at the same temperature for 1 h and allowed to come to room temperature. Removal of solvent in vacuo gave a residue which was subjected to flash chromatography on a silica gel column with acetone-hexane (1:1) as the eluent to provide the Fmoc protected tetrapeptide amide which was deprotected by stirring at room temperature with diethylamine (0.3 ml) in dichloromethane (10 ml) for 2 hr. The product was purified by flash chromatography on a silica gel column using acetone-hexane (1:4 to 7:3 gradient) to get the free amine as a white solid (29a, 0.24 g, 54%); $R_f$=0.21 (1:1 acetone-hexane); $[\alpha]_D^{25}$=−20° (c 0.38, methanol); mP 83–86° C.; IR(thin film): 3306, 2965, 2920, 2876, 2832, 1622, 1518, 1451, 1418, 1385, 1202, 1099, 1036 cm$^{-1}$; $^1$H NMR (500 MHz, CDCl₃): 6.97(d), 6.60(d), 6.37(m), 4.77(m), 3.35(t), 3.30(s), 3.13(s), 3.01(s), 2.68(t), 2.25(s); MS(m/z): 716(M⁺), 673, 628, 525, 481, 449, 390, 227, 186, 170, 154, 119, 100(100%).

This procedure is depicted in Scheme IX.

TABLE 11

Physical constants and spectroscopic data for the dolastatin 10 structural modifications 29a–l

| no. | n | R₆ | R₇ | R₄ | R₃ | R₁, R₂ | yield % | mp ° C. | $R_f$ | $[\alpha]_D^{25}$ °Chloroform | ir, $\nu_{max}$, cm$^{-1}$ | $^1$H nmr, δ | ms, M⁺ |
|---|---|---|---|---|---|---|---|---|---|---|---|---|---|
| 29a | 1 | H | a | Pr$^i$ | Pr$^i$ | Me | 33 | 100–105 | 0.34 (5:1 dichloromethane-methanol) | −132 (c 0.05) | 3511 1620 | 3.53, 3.51, 3.49, 3.24, 2.38 | 748 |
| 29b | 1 | H | b | Pr$^i$ | Pr$^i$ | Me | 77 | 73–76 | 0.32 (1:1 acetone-hexane) | −30.6 (c 0.17) | 3295 1686 1624 | 10.18, 8.8 8.14, 7.48 4.76, 3.52 3.48, 3.37 3.27, 2.98 2.23 | 724 |
| 29c | 1 | H | d | Pr$^i$ | Pr$^i$ | Me | 56 | 77–80 | 0.11 (1:1 acetone-hexane) | −38.6 (c 0.5, methanol) | 3165 1620 | 4.76, 3.55 3.37, 3.19 3.03, 2.34 1.38 | 721 |
| 29e | 1 | H | g | Bu$^s$ | Pr$^i$ | Me | 62 | 85 | 0.16 (1:1 acetone-hexane) | −16.3 (c 0.08, methanol) | 3306 1622 | 6.98, 6.60 4.80, 3.36 3.30, 3.02 2.71, 2.24 | 730 |
| 29f | 1 | H | g | Pr$^i$ | Pr$^i$ | Me | 91 | — | 0.27 (1:1 acetone-hexane) | −20.0 (c 0.09, methanol) | 3308 1676 | 7.58, 7.11 4.70, 3.75 3.48, 3.42 2.98, 2.80 2.23 | 716 |
| 29g | 1 | H | h | Pr$^i$ | Pr$^i$ | Me | 38 | 101–105 | 0.19 (1:1 acetone-hexane) | −13.3 (c 0.09, methanol) | 3291 1620 | 8.61, 7.2 7.02, 6.8 4.74, 3.81 3.31, 3.3 2.97, 2.25 | 770 |
| 29h | 1 | H | h | Bu$^s$ | Pr$^i$ | Me | 38 | 105 | 0.2 (1:1 acetone-hexane) | −8.0 (c 0.1, methanol) | 3289 1678 1626 | 8.42, 7.20 7.02, 6.8 4.8, 3.82 3.31, 3.3 2.29 | 752 M⁺-MeOH |

TABLE 11-continued

Physical constants and spectroscopic data for the dolastatin 10 structural modifications 29a–l

| no. | n | $R_6$ | $R_7$ | $R_4$ | $R_3$ | $R_1, R_2$ | yield % | mp °C. | $R_f$ | $[\alpha]_D^{25}$ °Chloroform | ir, $\nu_{max}$, cm$^{-1}$ | $^1$H nmr, δ | ms, M$^+$ |
|---|---|---|---|---|---|---|---|---|---|---|---|---|---|
| 29i | 1 | i | COOMe | Pr$^i$ | Pr$^i$ | Me | 66 | 61–65 | 0.6 (3:1 acetone-hexane) | −15.3 (c 0.15) | 3297 1748 1622 | 3.73, 3.68 3.37, 3.35 3.32, 3.29 3.12, 2.99 2.23 | 766 |
| 29j | 1 | PhCH$_2$ | c | Bu$^s$ | Pr$^i$ | Et | 82 | 65–70 | 0.66 (2:1 acetone-hexane) | −55.0 (c 0.06) | 3293 1626 | 7.71–7.74, 7.17–7.26, 5.52–5.65, 4.99, 3.39 3.35, 3.32 3.31, 2.98 | 826 |
| 29k | 1 | PhCH$_2$ | c | Bu$^s$ | Bu$^i$ | Me | 82 | 68–75 | 0.51 (3:2 acetone-hexane) | −61.8 (c 0.11) | 3291 1643 | 7.71, 3.37 3.33, 2.96 | 812 |
| 29l | 2 | NR$_6$R$_7$= | f | Pr$^i$ | Pr$^i$ | Me | 86 | 112–115 | 0.45 (9:1 methanol CHCl$_3$) | −65.8 (c 0.12) | 3380 1655 1640 1628 | 3.40, 3.37 3.30, 3.12 2.99 | 1246 |

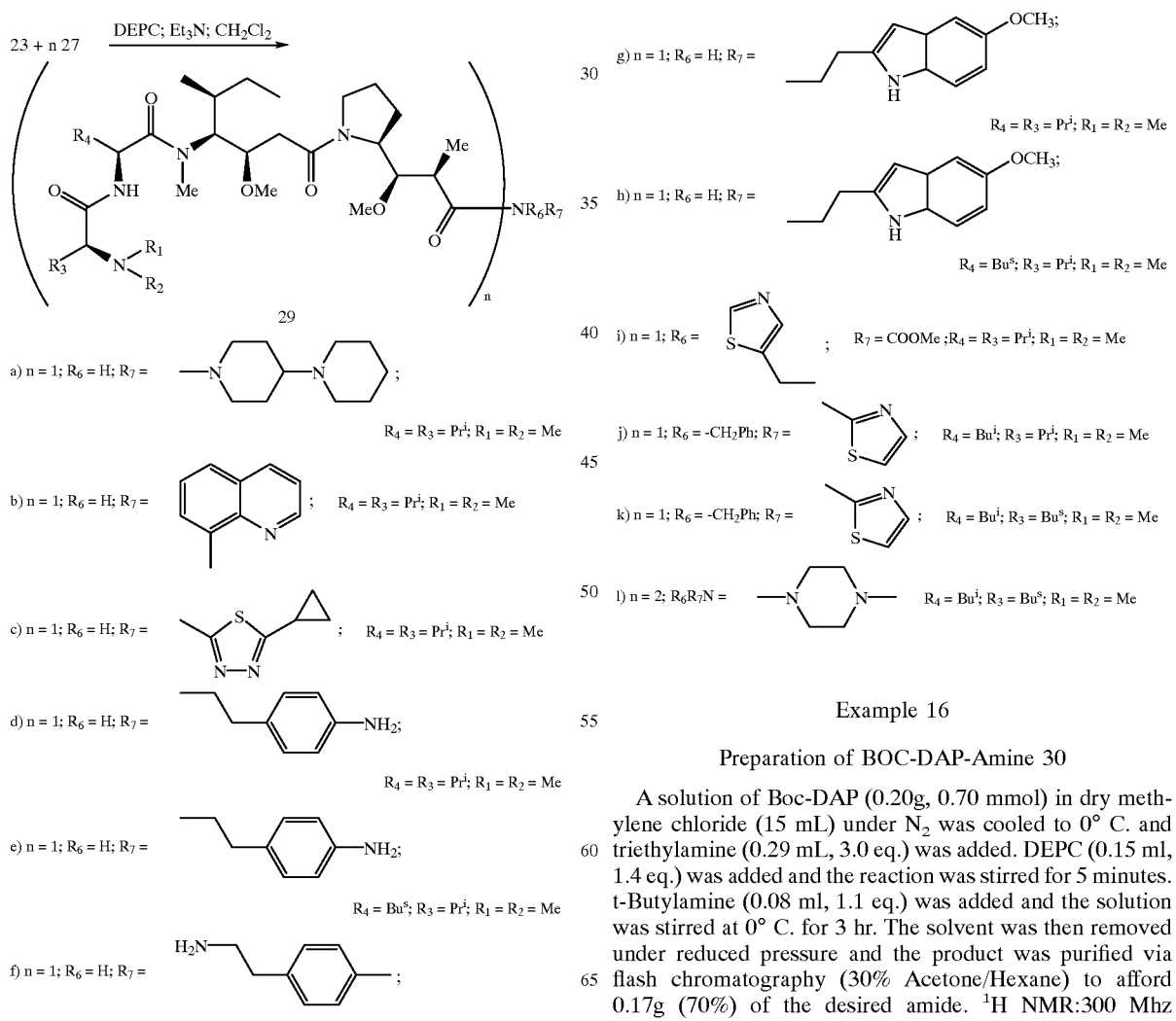

Scheme IX

Example 16

Preparation of BOC-DAP-Amine 30

A solution of Boc-DAP (0.20g, 0.70 mmol) in dry methylene chloride (15 mL) under N$_2$ was cooled to 0° C. and triethylamine (0.29 mL, 3.0 eq.) was added. DEPC (0.15 ml, 1.4 eq.) was added and the reaction was stirred for 5 minutes. t-Butylamine (0.08 ml, 1.1 eq.) was added and the solution was stirred at 0° C. for 3 hr. The solvent was then removed under reduced pressure and the product was purified via flash chromatography (30% Acetone/Hexane) to afford 0.17g (70%) of the desired amide. $^1$H NMR:300 Mhz (CDCl$_3$) δ 6.31 (bs, 1H), 4.21 (m, 1H), 3.44 (s, 3H), 3.40 (m, 1H), 3.32–3.21 (m, 2H), 2.01–1.65 (m, 5H), 1.43 (m, 9H), 1.38 (s, 9H), 1.21 (bd, 3H). Mass spectrum: $C_{18}H_{34}N_2O_4$ 310 ($M^+$—MeOH), 269, 263, 210, 170, 154, 114, 110, 86, 84, 70 (100), 58, 50, 42. IR (neat): 3351, 2976, 2936, 2882, 1694, 1535, 1454, 1393, 1370, 1285, 1258, 1167 $cm^{-1}$. Rotation:–37 (C=1.8 mg, MeOH)

Preparation of DOV-VAL-DIL-DAP-t-butylamide 31

Boc-DAP-t-butylamide 17 (0.19 g, 0.54 mmol) was dissolved in anhydrous methylene chloride (1 mL) under $N_2$ and cooled to 0° C. Trifluoroacetic acid (1 ml) was added and the solution was stirred at 0° C. for 2 hours. The solvents were removed under a stream of $N_2$ after warming to room temperature and the remaining residue was desiccated under vacuum for 2 hours. Tripeptide (1.0 eq., DOV-VAL-DIL-OtBu) was deprotected concurrently using the same procedure.

The resulting salts were combined in 5 mL of anhydrous methylene chloride under $N_2$. The solution was cooled to 0° C. and triethylamine (0.23 mL, 3.0 eq.) was added followed by diethylcyanophosphonate (0.11 mL, 1.3 eq.). The solution was stirred at 0° C. for 1 hour and then allowed to warm to room temperature and stirred an additional 2 hours. The mixture was concentrated under reduced pressure and chromatographed over silica gel (9:1 $CH_2Cl_2$/MeOH) to furnish the desired derivative 0.08 g (23%). Mass spectrum: $C_{35}H_{67}O_6N_5$ 653 ($M^+$), 638, 610, 578, 525, 481, 449, 428, 327, 227, 199, 186, 154, 128, 100 (100), 85. IR (neat): 3306, 2965, 2932, 2876, 1622, 1535, 1452, 1416, 1366, 1200, 1099 $cm^{-1}$. Rotation:–46 (C=1.2 mg, MeOH). mP. 120–125° C.

Example 17

Preparation of Boc-dolaproine-isopropyl Amide, 32

To a solution of Boc-Dap (145 mg, 0.51 mmol) in methylene chloride (10 mL) cooled to 0 ° C. was added HOBt (75 mg), EDC (105 mg) and triethylainine (85 μl). After 1 hr, isopropylamine (50 μl) was added and the solution was stirred for 1 hr at 0° C., followed by 15 hr at room temp. The thin layer chromatogram of the reaction mixture (2:3 ethyl acetate-hexane) indicated the formation of the product ($R_f$0.21). The reaction was diluted with methylene chloride (5 ml), washed successively with 10% citric acid (10 ml), water (10 ml), satd $NaHCO_3$ solution (10 ml), and water (10 ml) and dried over anhydrous $MgSO_4$. The thin layer chromatogram of the solution indicated a single product which was collected by concentrating the solution and drying under vacuum. Yield was 120 mg (72%); $[\alpha]_D^{25}$–44.4° (c, 0.378, $CHCl_3$).

Preparation of Dov-Val-Dil-Dap-isopropylamide, 33

A stirred solution of Boc-Dap-isopropylamide (33 mg, 0.1 mmol) in methylene chloride (1 mL) and trifluoroacctic acid (1 ml) in an ice bath was allowed to react for 2 hr, then solvents were removed in vacito. The residue was dissolved in toluene and reconcentrated. The TFA salt was dried under vacuum for 24 hr. Tripeptide (Dov-Val-Dil-OtBu 54.3 mg) was deprotected concurrently using the same procedure.

The resulting salts were combined in methylene chloride (2 mL) and cooled to 0° C. Triethylamine (50 μL) was added followed by diethylcyano phosphonate (23 μL). The solution was stirred at 0° C. for 2 hr. Solvents were removed under vacuum and the residue was chromatographed on silica gel (8:1 $CH_2Cl_2$-MeOH) to provide a pale yellow solid, 60 mg (96% yield): $[\alpha]_D^{25}$–47.10° (c, 0.104, $CHCl_3$), m.p. 70–73 ° C, $R_f$0.37 (3:2 acetone-hexane).

Preparation of BOC-DAP-Amine 20

A solution of Boc-DAP (0.21 g, 0.71 mmol) in dry methylene chloride (15 ml) under $N_2$ was cooled to 0c and triethylamine (0.25 ml, 2.5 eq.) was added. DEPC (0.15 g, 1.4 eq.) was added and the reaction was stirred for 5 minutes. Methylamine (0.43 ml of a 2.0 M solution in $CH_2Cl_2$, 1.2 eq.) was added and the solution was stirred at 0° C. for 2 hours. The solvent was removed under reduced pressure and the product was purified via flash chromatography (20% Acetone/Hexane) to afford 0.19 g (90%) of the desired amide. Mass spectrum: $C_{15}H_{28}N_2O_4$ 268 ($M^+$—MeOH), 227, 210, 170, 168, 157, 154, 131, 116, 114, 110, 100, 73, 70 (100), 58. IR (neat) 3308, 2974, 2936, 2880, 1694, 1651, 1549, 1456, 1402, 1366, 1254, 1167, 1105 $cm^{-1}$. Rotation: –26 (C=1.8 mg, MeOH).

Preparation of Dov-Val-Dil-Dap-methylamide 35

Boc-DAP-methylamide (0.10 g, 0.32 mmol) was dissolved in anhydrous methylene chloride (1 mL) under $N_2$ and cooled to 0° C. Trifluoroacetic acid (1 mL) was added and the solution was stirred at 0° C. for 2 hours. The solvents were removed under a stream of $N_2$ after warming to room temperature and the remaining residue was desiccated under vacuum for 2 hours. Tripeptide (1.0 dq., Dov-Val-Dil-OtBu) was deprotected concurrently using the same procedure.

The resulting salts were combined in 5 mL of anhydrous methylene chloride under $N_2$. The solution was cooled to 0° C. and triethylamine (0.14 ml, 3.0 eq.) was added followed by diethylcyanophosphonate (0.06 ml, 1.3 eq.). The solution was stirred at 0° C. for 1 hour and then allowed to warm to room temperature and stirred an additional 1 hour. The mixture was concentrated under reduced pressure and chromatographed over silica gel (9:1 $CH_2Cl_2$/MeOH) to furnish the desired derivative, 0.16 g (82%). Mass spectrum: $C_{32}H_{61}O_6N_5$ 611 ($M^+$), 596, 580, 568, 536, 525, 481, 449, 412, 386, 285, 255, 227, 199, 186, 170, 154, 128, 100 (100). IR (neat): 3304, 2963, 2936, 2876, 2832, 2789, 1622, 1532, 1452, 1416, 1200, 1099 $cm^{-1}$. Rotation: –27 (C=1.3 mg, MeOH).

Example 18

In vitro Evaluation of Compounds 12, 13, 28 and 29

Compounds prepared according to Examples 1–14 above were evaluated for in vitro cytotoxicity against a panel of cultured cancer cells, including the cell lines OVCAR-3 (ovarian cancer), SF-295 (central nervous system), A498 (renal cancer), NCI-H460 (non-small lung carcinoma), KM20L2 (colon cancer) and SK-MEL-5 (melanoma). For each cell line, each compound was tested at 5 concentrations, 100 μg/mL, 10 μg/mL, 1 μg/mL, 0.1 μg/mL and 0.01 μg/mL. Percent growth values were calculated for each concentration, and the two or three concentrations with growth values above, below or near 50% growth (relative to control) were used to calculate the $ED_{50}$ value using a linear regression calculation. In cases in which 50% growth inhibition was not observed for any of the concentrations, the $ED_{50}$ value was expressed as $ED_{50}$ >100 μg/mL. If the growth inhibition was greater than 50% for each concentration, the $ED_{50}$ was expressed as <0.01 μg/mL. Similar calculations were performed for total growth inhibition (TGI; 0% growth) and $LC_{50}$ (–50% growth).

At the start of each experiment, cells from the in vitro cell culture were inoculated into tubes or microtiter plates. One set of control tubes/plates was immediately counted to determine the cell count at the beginning of the experiment. This is the "baseline count" or $T_0$ reading. After 48 hours, a second set of control tubes/plates is analyzed to determine the control growth value. The growth or death of cells relative to the $T_0$ value is used to define the percent growth. The in vitro activity data for compounds 12, 13, 28 and 29 are presented in Tables 11 and 12.

TABLE 12

Human Cancer and Murine P-388 Lymphocytic Leukemia ($ED_{50}$) Cell Line inhibitory Results for Peptides 12 & 13

| Cell type | Cell line | | 12a | 12b | 12c | 12d | 12e | 13a | 13b |
|---|---|---|---|---|---|---|---|---|---|
| Ovarian | OVCAR-3 | GI-50 | $3.5 \times 10^{-4}$ | $3.0 \times 10^{-4}$ | $<1 \times 10^{-4}$ | $3.1 \times 10^{-4}$ | $3.5 \times 10^{-3}$ | $8.3 \times 10^{-4}$ | $3.5 \times 10^{-4}$ |
| CNS | SF-295 | ($\mu$g/ml) | $1.1 \times 10^{-3}$ | $3.6 \times 10^{-4}$ | $1.1 \times 10^{-2}$ | $4.7 \times 10^{-4}$ | $4.3 \times 10^{-2}$ | $>1 \times 10^{-2}$ | $5.2 \times 10^{-4}$ |
| Renal | A498 | | $5.8 \times 10^{-4}$ | $3.3 \times 10^{-4}$ | $6.1 \times 10^{-3}$ | $4.8 \times 10^{-4}$ | $2.9 \times 10^{-2}$ | $3.4 \times 10^{-3}$ | $2.0 \times 10^{-3}$ |
| Lung-NSC | NCI-H460 | | $4.9 \times 10^{-4}$ | $3.3 \times 10^{-4}$ | $4.2 \times 10^{-5}$ | $2.9 \times 10^{-4}$ | $2.3 \times 10^{-2}$ | $2.9 \times 10^{-3}$ | $4.7 \times 10^{-4}$ |
| Colon | KM20L2 | | $3.8 \times 10^{-4}$ | $3.7 \times 10^{-4}$ | $1.3 \times 10^{-4}$ | $3.0 \times 10^{-4}$ | $9.1 \times 10^{-4}$ | $2.6 \times 10^{-3}$ | $3.6 \times 10^{-4}$ |
| Melanoma | SK-MEL-5 | | $2.9 \times 10^{-4}$ | $4.6 \times 10^{-4}$ | $4.0 \times 10^{-5}$ | $4.4 \times 10^{-4}$ | $4.5 \times 10^{-4}$ | $1.1 \times 10^{-3}$ | $7.0 \times 10^{-4}$ |
| Ovarian | OVCAR-3 | TGI | $1.8 \times 10^{-3}$ | $>1 \times 10^{-2}$ | $2.1 \times 10^{-3}$ | $>1 \times 10^{-2}$ | $1.0 \times 10^{-1}$ | $>1 \times 10^{-2}$ | $3.4 \times 10^{-3}$ |
| CNS | SF-295 | ($\mu$g/ml) | $>1 \times 10^{-2}$ | $>1 \times 10^{-2}$ | $>1 \times 10^{-2}$ | $>1 \times 10^{-2}$ | $>10$ | $>1 \times 10^{-2}$ | $>1 \times 10^{-2}$ |
| Renal | A498 | | $>1 \times 10^{-2}$ | $>1 \times 10^{-2}$ | $>1 \times 10^{-2}$ | $>1 \times 10^{-2}$ | $>10$ | $>1 \times 10^{-2}$ | $>1 \times 10^{-2}$ |
| Lung-NSC | NCI-H460 | | $>1 \times 10^{-2}$ | $>1 \times 10^{-2}$ | $>1 \times 10^{-2}$ | $4.0 \times 10^{-3}$ | $1.1$ | $>1 \times 10^{-2}$ | $>1 \times 10^{-2}$ |
| Colon | KM20L2 | | $>1 \times 10^{-2}$ | $>1 \times 10^{-2}$ | $>1 \times 10^{-2}$ | $9.0 \times 10^{-4}$ | $7.2 \times 10^{-1}$ | $>1 \times 10^{-2}$ | $>1 \times 10^{-2}$ |
| Melanoma | SK-MEL-5 | | $>1 \times 10^{-2}$ | $>1 \times 10^{-2}$ | $>1 \times 10^{-2}$ | $>1 \times 10^{-2}$ | $>10$ | $>1 \times 10^{-2}$ | $>1 \times 10^{-2}$ |
| Ovarian | OVCAR-3 | LC-50 | $>1 \times 10^{-2}$ | $>1 \times 10^{-2}$ | $>1$ | $>1 \times 10^{-2}$ | $>10$ | $>1 \times 10^{-2}$ | $>1 \times 10^{-2}$ |
| CNS | SF-295 | ($\mu$g/ml) | $>1 \times 10^{-2}$ | $>1 \times 10^{-2}$ | $>1$ | $>1 \times 10^{-2}$ | $>10$ | $>1 \times 10^{-2}$ | $>1 \times 10^{-2}$ |
| Renal | A498 | | $>1 \times 10^{-2}$ | $>1 \times 10^{-2}$ | $>1$ | $>1 \times 10^{-2}$ | $>10$ | $>1 \times 10^{-2}$ | $>1 \times 10^{-2}$ |
| Lung-NSC | NCI-H460 | | $>1 \times 10^{-2}$ | $>1 \times 10^{-2}$ | $>1$ | $>1 \times 10^{-2}$ | $>10$ | $>1 \times 10^{-2}$ | $>1 \times 10^{-2}$ |
| Colon | KM20L2 | | $>1 \times 10^{-2}$ | $>1 \times 10^{-2}$ | $>1$ | $>1 \times 10^{-2}$ | $>10$ | $>1 \times 10^{-2}$ | $>1 \times 10^{-2}$ |
| Melanoma | SK-MEL-5 | | $>1 \times 10^{-2}$ | $>1 \times 10^{-2}$ | $>1$ | $>1 \times 10^{-2}$ | $>10$ | $>1 \times 10^{-2}$ | $>1 \times 10^{-2}$ |
| Mouse Leukemia | P-388 | ED50 ($\mu$g/ml) | $4.4 \times 10^{-3}$ | $4.0 \times 10^{-3}$ | $3.0 \times 10^{-1}$ | $<1 \times 10^{-4}$ | $3.0 \times 10^{-1}$ | $7.2 \times 10^{-3}$ | $2.2 \times 10^{-3}$ |

| Cell type | Cell line | | 13c | 13d | 13e | 13f | 13g |
|---|---|---|---|---|---|---|---|
| Ovarian | OVCAR-3 | GI-50 | $3.1 \times 10^{-4}$ | $2.7 \times 10^{-3}$ | $1.3 \times 10^{-3}$ | $1.2 \times 10^{-3}$ | $2.3 \times 10^{-2}$ |
| CNS | SF-295 | ($\mu$g/ml) | $1.7 \times 10^{-3}$ | $>1 \times 10^{-2}$ | $4.9 \times 10^{-4}$ | $2.6 \times 10^{-3}$ | $3.5 \times 10^{-2}$ |
| Renal | A498 | | $6.9 \times 10^{-4}$ | $>1 \times 10^{-2}$ | $3.4 \times 10^{-3}$ | $5.2 \times 10^{-3}$ | $5.6 \times 10^{-2}$ |
| Lung-NSC | NCI-H460 | | $3.7 \times 10^{-4}$ | $3.9 \times 10^{-2}$ | $2.7 \times 10^{-3}$ | $3.6 \times 10^{-3}$ | $3.1 \times 10^{-2}$ |
| Colon | KM20L2 | | $3.3 \times 10^{-4}$ | $3.6 \times 10^{-3}$ | $3.1 \times 10^{-4}$ | $4.5 \times 10^{-4}$ | $2.3 \times 10^{-2}$ |
| Melanoma | SK-MEL-5 | | $2.2 \times 10^{-4}$ | $5.6 \times 10^{-5}$ | $2.0 \times 10^{-3}$ | $2.3 \times 10^{-3}$ | $3.5 \times 10^{-2}$ |
| Ovarian | OVCAR-3 | TGI | $1.8 \times 10^{-3}$ | $>1 \times 10^{-2}$ | $6.5 \times 10^{-3}$ | $2.5 \times 10^{-2}$ | $1.3 \times 10^{-1}$ |
| CNS | SF-295 | ($\mu$g/ml) | $>1 \times 10^{-2}$ | $>1 \times 10^{-2}$ | $>1 \times 10^{-2}$ | $>1$ | $>1$ |
| Renal | A498 | | $>1 \times 10^{-2}$ | $>1 \times 10^{-2}$ | $>1 \times 10^{-2}$ | $>1$ | $>1$ |
| Lung-NSC | NCI-H460 | | $>1 \times 10^{-2}$ | $>1 \times 10^{-2}$ | $>1 \times 10^{-2}$ | $>1$ | $>1$ |
| Colon | KM20L2 | | $>1 \times 10^{-2}$ | $>1 \times 10^{-2}$ | $>1 \times 10^{-2}$ | $1.1 \times 10^{-1}$ | $1.6 \times 10^{-1}$ |
| Melanoma | SK-MEL-5 | | $>1 \times 10^{-2}$ | $>1 \times 10^{-2}$ | $>1 \times 10^{-2}$ | $>1$ | $>1$ |
| Ovarian | OVCAR-3 | LC-50 | $>1 \times 10^{-2}$ | $>1 \times 10^{-2}$ | $>1 \times 10^{-2}$ | $>1$ | $>1$ |
| CNS | SF-295 | ($\mu$g/ml) | $>1 \times 10^{-2}$ | $>1 \times 10^{-2}$ | $>1 \times 10^{-2}$ | $>1$ | $>1$ |
| Renal | A498 | | $>1 \times 10^{-2}$ | $>1 \times 10^{-2}$ | $>1 \times 10^{-2}$ | $>1$ | $>1$ |
| Lung-NSC | NCI-H460 | | $>1 \times 10^{-2}$ | $>1 \times 10^{-2}$ | $>1 \times 10^{-2}$ | $>1$ | $>1$ |
| Colon | KM20L2 | | $>1 \times 10^{-2}$ | $>1 \times 10^{-2}$ | $>1 \times 10^{-2}$ | $>1$ | $>1$ |
| Melanoma | SK-MEL-5 | | $>1 \times 10^{-2}$ | $>1 \times 10^{-2}$ | $>1 \times 10^{-2}$ | $>1$ | $>1$ |
| Mouse Leukemia | P-388 | ED50 ($\mu$g/ml) | $2.5 \times 10^{-3}$ | $1.9 \times 10^{-1}$ | $4.8 \times 10^{-3}$ | $3.8 \times 10^{-2}$ | $3.5 \times 10^{-1}$ |

TABLE 13

Human Cancer-Cell line and P-388 Mouse Leukemia ($ED_{50}$) data for peptides 28a–g & 29a–l

| | Cell type | Cell Line | 28a | 28b | 28c | 28d | 28e | 28f | 28g |
|---|---|---|---|---|---|---|---|---|---|
| GI-50 ($\mu$g/ml) | Ovarian | OVCAR-3 | $3.1 \times 10^{-5}$ | $4.6 \times 10^{-5}$ | $4.9 \times 10^{-5}$ | $3.0 \times 10^{-7}$ | $3.6 \times 10^{-5}$ | $1.8 \times 10^{-5}$ | $9.1 \times 10^{-4}$ |
| | CNS | SF-295 | $1.9 \times 10^{-4}$ | $3.8 \times 10^{-4}$ | $4.7 \times 10^{-4}$ | $6.1 \times 10^{-7}$ | $5.9 \times 10^{-5}$ | $>1.0 \times 10^{-4}$ | $>1 \times 10^{-2}$ |
| | Renal | A498 | $3.8 \times 10^{-4}$ | $3.9 \times 10^{-4}$ | $2.2 \times 10^{-4}$ | $3.4 \times 10^{-6}$ | $5.3 \times 10^{-4}$ | $>1.0 \times 10^{-4}$ | $3.0 \times 10^{-3}$ |
| | Lung-NSC | NCI-H460 | $1.1 \times 10^{-4}$ | $5.5 \times 10^{-4}$ | $4.0 \times 10^{-4}$ | $4.1 \times 10^{-7}$ | $1.9 \times 10^{-5}$ | $3.3 \times 10^{-5}$ | $2.3 \times 10^{-3}$ |
| | Colon | KM20L2 | $1.5 \times 10^{-4}$ | $2.2 \times 10^{-4}$ | $4.5 \times 10^{-5}$ | $2.0 \times 10^{-7}$ | $3.2 \times 10^{-6}$ | $2.2 \times 10^{-5}$ | $2.4 \times 10^{-3}$ |
| | Melanoma | SK-MEL-5 | $4.7 \times 10^{-5}$ | $7.0 \times 10^{-4}$ | $3.7 \times 10^{-5}$ | $5.6 \times 10^{-7}$ | $2.0 \times 10^{-5}$ | $4.7 \times 10^{-6}$ | $4.4 \times 10^{-4}$ |
| TGI ($\mu$g/ml) | Ovarian | OVCAR-3 | $1.0 \times 10^{-3}$ | $7.0 \times 10^{-3}$ | $>1 \times 10^{-2}$ | $1.1 \times 10^{-5}$ | $7.9 \times 10^{-4}$ | $9.4 \times 10^{-5}$ | $>1 \times 10^{-2}$ |
| | CNS | SF-295 | $>1 \times 10^{-2}$ | $>1 \times 10^{-2}$ | $>1 \times 10^{-2}$ | $>1 \times 10^{-4}$ | $>1 \times 10^{-2}$ | $>1 \times 10^{-4}$ | $>1 \times 10^{-2}$ |
| | Renal | A498 | $>1 \times 10^{-2}$ | $>1 \times 10^{-2}$ | $>1 \times 10^{-2}$ | $>1 \times 10^{-4}$ | $>1 \times 10^{-2}$ | $>1 \times 10^{-4}$ | $>1 \times 10^{-2}$ |
| | Lung-NSC | NCI-H460 | $>1 \times 10^{-2}$ | $>1 \times 10^{-2}$ | $>1 \times 10^{-2}$ | $>1 \times 10^{-4}$ | $2.3 \times 10^{-4}$ | $>1 \times 10^{-4}$ | $>1 \times 10^{-2}$ |
| | Colon | KM20L2 | $>1 \times 10^{-2}$ | $>1 \times 10^{-2}$ | $>1 \times 10^{-2}$ | $4.1 \times 10^{-6}$ | $2.1 \times 10^{-4}$ | $>1 \times 10^{-4}$ | $>1 \times 10^{-2}$ |
| | Melanoma | SK-MEL-5 | $>1 \times 10^{-2}$ | $>1 \times 10^{-2}$ | $>1 \times 10^{-2}$ | $>1 \times 10^{-4}$ | $>1 \times 10^{-2}$ | $>1 \times 10^{-4}$ | $>1 \times 10^{-2}$ |
| LC-50 ($\mu$g/ml) | Ovarian | OVCAR-3 | $>1 \times 10^{-2}$ | $>1 \times 10^{-2}$ | $>1 \times 10^{-2}$ | $>1 \times 10^{-4}$ | $>1 \times 10^{-2}$ | $>1 \times 10^{-4}$ | $>1 \times 10^{-2}$ |
| | CNS | SF-295 | $>1 \times 10^{-2}$ | $>1 \times 10^{-2}$ | $>1 \times 10^{-2}$ | $>1 \times 10^{-4}$ | $>1 \times 10^{-2}$ | $>1 \times 10^{-4}$ | $>1 \times 10^{-2}$ |
| | Renal | A498 | $>1 \times 10^{-2}$ | $>1 \times 10^{-2}$ | $>1 \times 10^{-2}$ | $>1 \times 10^{-4}$ | $>1 \times 10^{-2}$ | $>1 \times 10^{-4}$ | $>1 \times 10^{-2}$ |

TABLE 13-continued

Human Cancer-Cell line and P-388 Mouse Leukemia ($ED_{50}$) data for peptides 28a–g & 29a–l

| | | | | | | | | | |
|---|---|---|---|---|---|---|---|---|---|
| | Lung-NSC | NCI-H460 | $>1 \times 10^{-2}$ | $>1 \times 10^{-2}$ | $>1 \times 10^{-2}$ | $>1 \times 10^{-4}$ | $>1 \times 10^{-2}$ | $>1 \times 10^{-4}$ | $>1 \times 10^{-2}$ |
| | Colon | KM20L2 | $>1 \times 10^{-2}$ | $>1 \times 10^{-2}$ | $>1 \times 10^{-2}$ | $>1 \times 10^{-4}$ | $>1 \times 10^{-2}$ | $>1 \times 10^{-4}$ | $>1 \times 10^{-2}$ |
| | Melanoma | SK-MEL-5 | $>1 \times 10^{-2}$ | $>1 \times 10^{-2}$ | $>1 \times 10^{-2}$ | $>1 \times 10^{-4}$ | $>1 \times 10^{-2}$ | $>1 \times 10^{-4}$ | $>1 \times 10^{-2}$ |
| ED50 ($\mu$g/ml) | Mouse Leukemia | P-388 | $<1.0 \times 10^{-3}$ | $1.96 \times 10^{-3}$ | $2.03 \times 10^{-3}$ | $2.55 \times 10^{-6}$ | $8.22 \times 10^{-5}$ | $2.12 \times 10^{-2}$ | $2.05 \times 10^{-2}$ |

| | Cell type | Cell Line | 29a | 29b | 29c | 29d | 29e | 29f | 29g |
|---|---|---|---|---|---|---|---|---|---|
| GI-50 ($\mu$g/ml) | Ovarian | OVCAR-3 | $3.2 \times 10^{-3}$ | $2.5 \times 10^{-3}$ | $3.6 \times 10^{-2}$ | $5.0 \times 10^{-5}$ | $<1.0 \times 10^{-4}$ | $3.6 \times 10^{-2}$ | $<1.0 \times 10^{-4}$ |
| | CNS | SF-295 | $3.6 \times 10^{-2}$ | $1.5 \times 10^{-3}$ | $4.8 \times 10^{-2}$ | $5.3 \times 10^{-4}$ | $2.1 \times 10^{-4}$ | $2.1 \times 10^{-1}$ | $<1.0 \times 10^{-4}$ |
| | Renal | A498 | $8.1 \times 10^{-3}$ | $8.8 \times 10^{-3}$ | $1.0 \times 10^{-1}$ | $>1 \times 10^{-2}$ | $9.4 \times 10^{-4}$ | $1.1 \times 10^{-1}$ | $<1.0 \times 10^{-4}$ |
| | Lung-NSC | NCI-H460 | $2.4 \times 10^{-3}$ | $2.9 \times 10^{-3}$ | $3.1 \times 10^{-2}$ | $1.3 \times 10^{-4}$ | $7.5 \times 10^{-5}$ | $1.1 \times 10^{-1}$ | $<1.0 \times 10^{-4}$ |
| | Colon | KM20L2 | $3.0 \times 10^{-3}$ | $1.4 \times 10^{-3}$ | $1.4 \times 10^{-2}$ | $4.9 \times 10^{-5}$ | $<1.0 \times 10^{-4}$ | $4.0 \times 10^{-2}$ | $<1.0 \times 10^{-4}$ |
| | Melanoma | SK-MEL-5 | $2.8 \times 10^{-3}$ | $3.6 \times 10^{-4}$ | $3.4 \times 10^{-2}$ | $2.3 \times 10^{-4}$ | $<1.0 \times 10^{-4}$ | $5.5 \times 10^{-2}$ | $<1.0 \times 10^{-4}$ |
| TGI ($\mu$g/ml) | Ovarian | OVCAR-3 | $1.1 \times 10^{-2}$ | $2.3 \times 10^{-2}$ | $2.9 \times 10^{-1}$ | $7.9 \times 10^{-4}$ | $1.4 \times 10^{-3}$ | $1.5 \times 10^{-1}$ | $<1.0 \times 10^{-4}$ |
| | CNS | SF-295 | $>1$ | $>1$ | $>10$ | $>1 \times 10^{-2}$ | $>1$ | $>1$ | $2.8 \times 10^{-1}$ |
| | Renal | A498 | $>1$ | $>1$ | $>10$ | $>1 \times 10^{-2}$ | $3.7 \times 10^{-1}$ | $>1$ | $3.4 \times 10$ |
| | Lung-NSC | NCI-H460 | $9.2 \times 10\text{-}3$ | $1.9 \times 10^{-1}$ | $1.5$ | $8.7 \times 10^{-4}$ | $81.1 \times 10^{-1}$ | $>1$ | $>1$ |
| | Colon | KM20L2 | $>1$ | $1.4 \times 10^{-1}$ | $1.1$ | $>1 \times 10^{-2}$ | $1.1 \times 10^{-1}$ | $>1$ | $1.7 \times 10^{-4}$ |
| | Melanoma | SK-MEL-5 | $>1$ | $>1$ | $>10$ | $>1 \times 10^{-2}$ | $>1$ | $>1$ | $>1$ |
| LC-50 ($\mu$g/ml) | Ovarian | OVCAR-3 | $>1$ | $>1$ | $>10$ | $>1 \times 10^{-2}$ | $>1$ | $>1$ | $>1$ |
| | CNS | SF-295 | $>1$ | $>1$ | $>10$ | $>1 \times 10^{-2}$ | $>1$ | $>1$ | $>1$ |
| | Renal | A498 | $>1$ | $>1$ | $>10$ | $>1 \times 10^{-2}$ | $>1$ | $>1$ | $>1$ |
| | Lung-NSC | NCI-H460 | $>1$ | $>1$ | $>10$ | $>1 \times 10^{-2}$ | $>1$ | $>1$ | $>1$ |
| | Colon | KM20L2 | $>1$ | $>1$ | $>10$ | $>1 \times 10^{-2}$ | $>1$ | $>1$ | $>1$ |
| | Melanoma | SK-MEL-5 | $>1$ | $>1$ | $>10$ | $>1 \times 10^{-2}$ | $>1$ | $>1$ | $>1$ |
| ED50 ($\mu$g/ml) | Mouse Leukemia | P-388 | $5.11 \times 10^{-2}$ | $3.53 \times 10^{-3}$ | $2.72 \times 10^{-1}$ | $3.38 \times 10^{-4}$ | $3.56 \times 10^{-3}$ | $4.01 \times 10^{-2}$ | $1.84 \times 10^{-3}$ |

| | Cell type | Cell Line | 29h | 29i | 29j | 29k | 29l |
|---|---|---|---|---|---|---|---|
| GI-50 ($\mu$g/ml) | Ovarian | OVCAR-3 | $<1.0 \times 10^{-4}$ | $3.4 \times 10^{-4}$ | $4.7 \times 10^{-5}$ | $3.1 \times 10^{-4}$ | $1.6 \times 10^{-2}$ |
| | CNS | SF-295 | $2.5 \times 10^{-4}$ | $2.6 \times 10^{-4}$ | $2.8 \times 10^{-4}$ | $4.0 \times 10^{-4}$ | $3.8 \times 10^{-1}$ |
| | Renal | A498 | $7.1 \times 10^{-4}$ | $>1 \times 10^{-3}$ | $2.7 \times 10^{-4}$ | $3.2 \times 10^{-4}$ | $8.4 \times 10^{-2}$ |
| | Lung-NSC | NCI-H460 | $1.1 \times 10^{-4}$ | $3.0 \times 10^{-4}$ | $1.0 \times 10^{-4}$ | $2.9 \times 10^{-4}$ | $3.0 \times 10^{-2}$ |
| | Colon | KM20L2 | $<1.0 \times 10^{-5}$ | $3.9 \times 10^{-5}$ | $4.7 \times 10^{-5}$ | $3.4 \times 10^{-5}$ | $3.4 \times 10^{-2}$ |
| | Melanoma | SK-MEL-5 | $<1.0 \times 10^{-4}$ | $1.5 \times 10^{-4}$ | $5.9 \times 10^{-5}$ | $2.3 \times 10^{-4}$ | $5.8 \times 10^{-3}$ |
| TGI ($\mu$g/ml) | Ovarian | OVCAR-3 | $3.2 \times 10^{-4}$ | $>1 \times 10^{-3}$ | $7.9 \times 10^{-4}$ | $>1 \times 10^{-2}$ | $1 \times 10^{-1}$ |
| | CNS | SF-295 | $2.8 \times 10^{-1}$ | $>1 \times 10^{-3}$ | $>1 \times 10^{-2}$ | $>1 \times 10^{-2}$ | $>1$ |
| | Renal | A498 | $3.1 \times 10^{-1}$ | $>1 \times 10^{-3}$ | $>1 \times 10^{-2}$ | $>1 \times 10^{-2}$ | $>1$ |
| | Lung-NSC | NCI-H460 | $>1$ | $8.8 \times 10^{-4}$ | $1.4 \times 10^{-3}$ | $8.4 \times 10^{-4}$ | $>1$ |
| | Colon | KM20L2 | $1.9 \times 10^{-2}$ | $>1 \times 10^{-3}$ | $>1 \times 10^{-2}$ | $1.0 \times 10^{-3}$ | $>1$ |
| | Melanoma | SK-MEL-5 | $>1$ | $>1 \times 10^{-3}$ | $>1 \times 10^{-2}$ | $>1 \times 10^{-2}$ | $>1$ |
| LC-50 ($\mu$g/ml) | Ovarian | OVCAR-3 | $>1$ | $>1 \times 10^{-3}$ | $>1 \times 10^{-2}$ | $>1 \times 10^{-2}$ | $>1$ |
| | CNS | SF-295 | $>1$ | $>1 \times 10^{-3}$ | $>1 \times 10^{-2}$ | $>1 \times 10^{-2}$ | $>1$ |
| | Renal | A498 | $>1$ | $>1 \times 10^{-3}$ | $>1 \times 10^{-2}$ | $>1 \times 10^{-2}$ | $>1$ |
| | Lung-NSC | NCI-H460 | $>1$ | $>1 \times 10^{-3}$ | $>1 \times 10^{-2}$ | $>1 \times 10^{-2}$ | $>1$ |
| | Colon | KM20L2 | $>1$ | $>1 \times 10^{-3}$ | $>1 \times 10^{-2}$ | $>1 \times 10^{-2}$ | $>1$ |
| | Melanoma | SK-MEL-5 | $>1$ | $>1 \times 10^{-3}$ | $>1 \times 10^{-2}$ | $>1 \times 10^{-2}$ | $>1$ |
| ED50 ($\mu$g/ml) | Mouse Leukemia | P-388 | $3.60 \times 10^{-3}$ | $2.73 \times 10^{-1}$ | $2.11 \times 10^{-4}$ | $<1 \times 10^{-4}$ | $1.66 \times 10^{-1}$ |

What is claimed is:

1. The compound of the formula

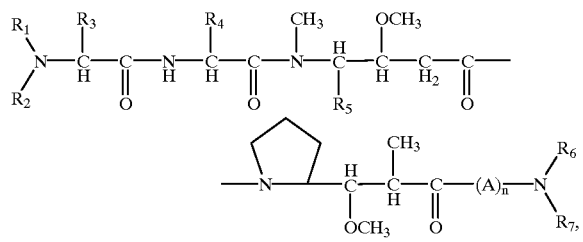

or a salt thereof with a pharmaceutically acceptable acid, wherein $R_1$–$R_5$ are each, independently, a hydrogen atom or a normal or branched $C_1$–$C_6$-alkyl group;

A is a phenylalanyl or phenylglycyl residue;

n is 0 or 1;

$R_6$ is a hydrogen atom; and $R_7$ is selected from the group consisting of t-butyl, isopropyl, methyl, 2-pyridylmethyl, 3-pyridylmethyl, 4-pyridylmethyl, 2-(3-pyridyl)ethyl, 4-pyridyl,

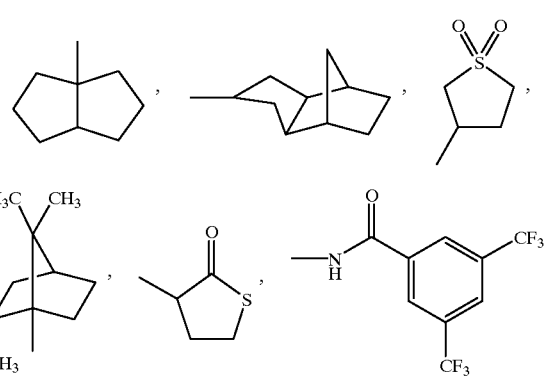

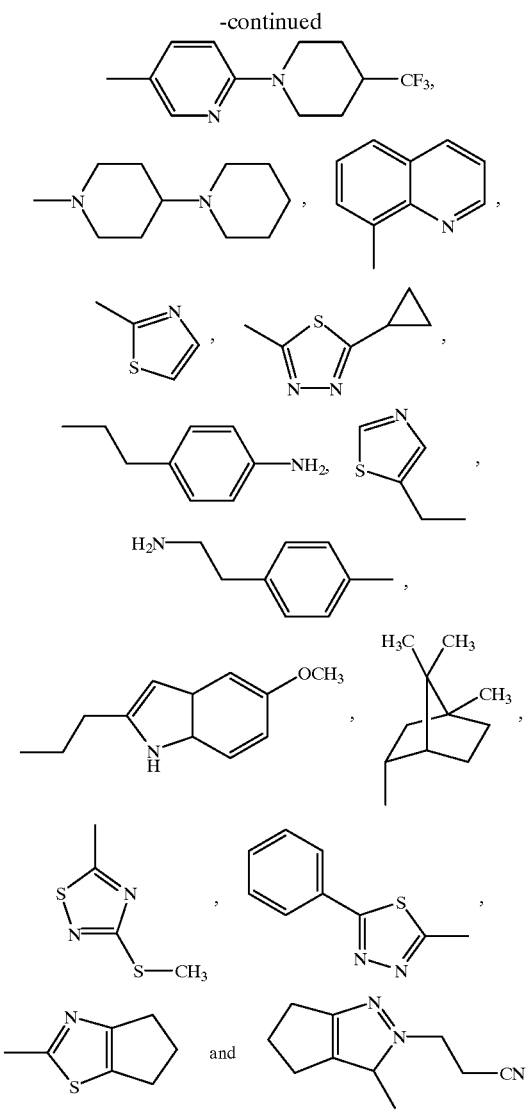

or

R$_6$ is benzyl or —C(O)OR$_8$, wherein R$_8$ is a C$_1$–C$_6$-alkyl group; and

R$_7$ is a 2-thiazolyl group.

2. The compound of claim 1 wherein R$_1$ and R$_2$ are each a methyl group, R$_3$ is an isopropyl or sec-butyl group, R$_4$ is an isopropyl, sec-butyl or isobutyl group, and R$_5$ is a sec-butyl group.

3. The compound of the formula

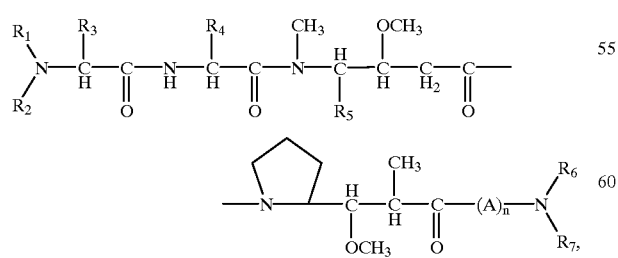

or a salt thereof with a pharmaceutically acceptable acid, wherein R$_1$ and R$_2$ are each methyl; R$_3$ and R$_4$ are each isopropyl; R$_5$ is sec-butyl; n is 1; A is a methionyl residue; R$_6$ is a hydrogen atom; and R$_7$ is selected from the group consisting of

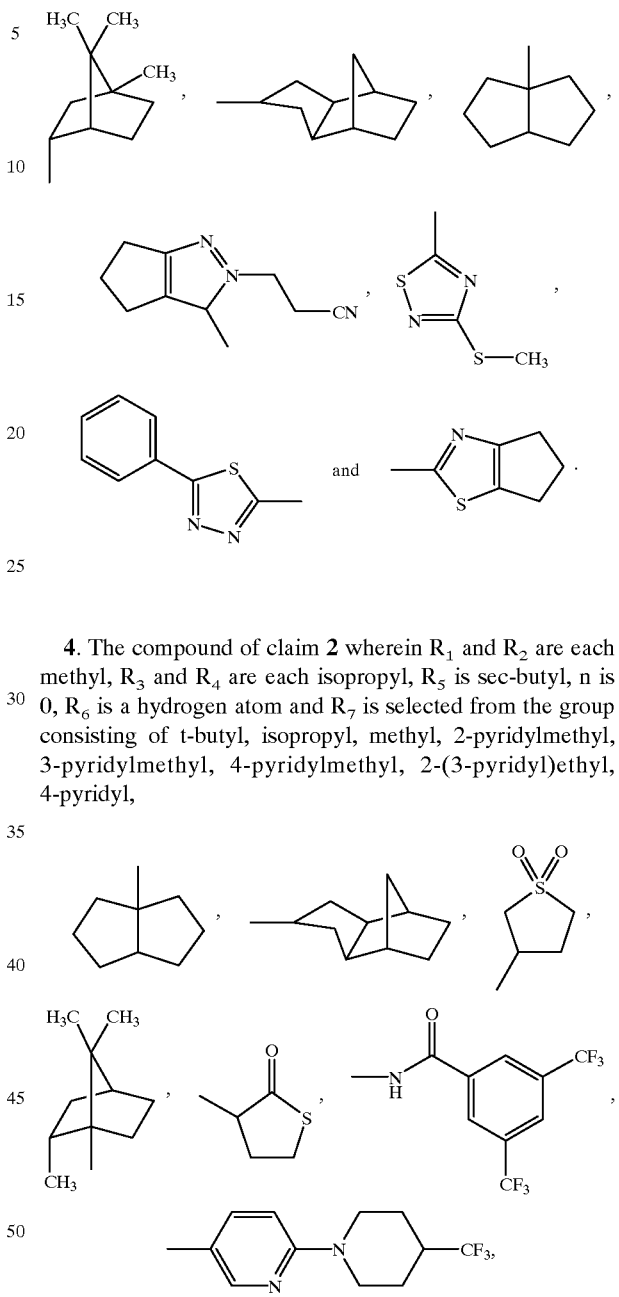

4. The compound of claim 2 wherein R$_1$ and R$_2$ are each methyl, R$_3$ and R$_4$ are each isopropyl, R$_5$ is sec-butyl, n is 0, R$_6$ is a hydrogen atom and R$_7$ is selected from the group consisting of t-butyl, isopropyl, methyl, 2-pyridylmethyl, 3-pyridylmethyl, 4-pyridylmethyl, 2-(3-pyridyl)ethyl, 4-pyridyl,

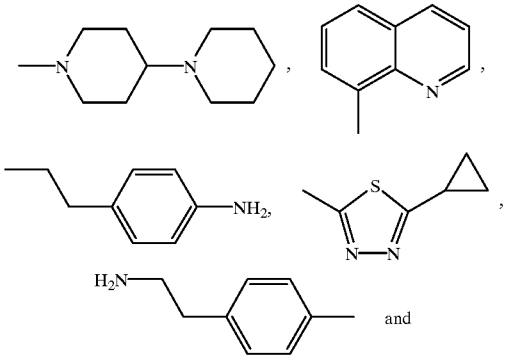

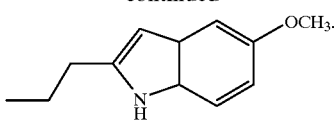

5. The compound of claim 2 wherein $R_1$ and $R_2$ are each methyl; $R_3$ is isopropyl; $R_4$ and $R_5$ are each sec-butyl; n is 0; $R_6$ is a hydrogen atom; and $R_7$ is

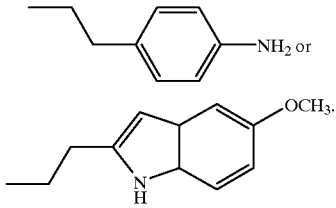

6. The compound of claim 2 wherein $R_1$ and $R_2$ are each methyl; $R_3$ is isopropyl; $R_4$ is isopropyl or sec-butyl; $R_5$ is sec-butyl; n is 0; $R_6$ is a benzyl group or —C(O)OCH$_3$; and $R_7$ is a 2-thiazolyl group.

7. The compound of claim 2 wherein $R_1$ and $R_2$ are each methyl; $R_3$ is isopropyl; $R_4$ is isopropyl; $R_5$ is sec-butyl; n is 1; A is a phenylalanyl residue; $R_6$ is a hydrogen atom; and $R_7$ is

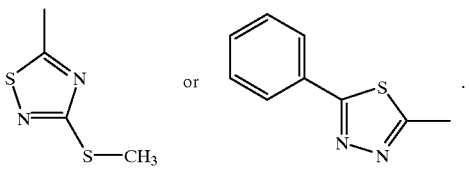

8. The compound of the formula

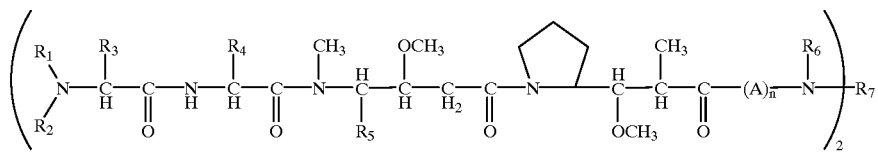

or a salt thereof with a pharmaceutically acceptable acid, wherein $R_1$–$R_5$ are each, independently, a hydrogen atom or a normal or branched $C_1$–$C_6$-alkyl group;

A is a methionyl, phenylalanyl or phenylglycyl residue;

n is 0 or 1;

$R_6$ is a hydrogen atom; and $R_7$ is an aromatic group.

9. The compound of claim 8 wherein $R_7$ is

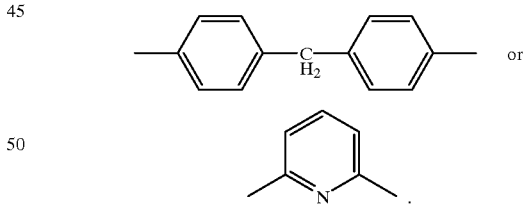

10. The compound of claim 9 wherein $R_1$ and $R_2$ are each a methyl group; $R_3$ and $R_4$ are each an isopropyl group; $R_5$ is a sec-butyl group; n is 1; and A is a methionyl residue.

11. A compound of the formula

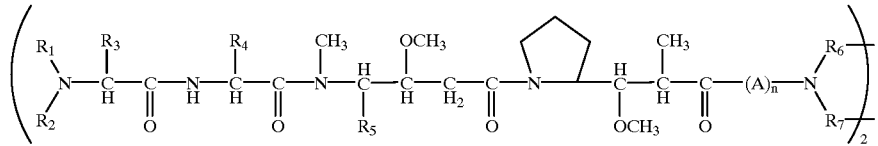

or a salt thereof with a pharmaceutically acceptable acid, wherein $R_1$–$R_5$ are each, independently, a hydrogen atom or a normal or branched $C_1$–$C_6$-alkyl group;

A is a methionyl, phenylalanyl or phenylglycyl residue;

n is 0 or 1; and

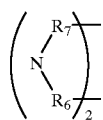

is a five-or six-membered ring.

12. The compound of claim 11 wherein $R_6$ and $R_7$ are each a methylene group.

13. The compound of claim 12 wherein $R_1$ and $R_2$ are each a methyl group; $R_3$ and $R_4$ are each an isopropyl group; $R_5$ is a sec-butyl group; and n is 0.

14. The compound of the formula

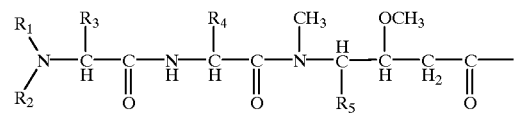

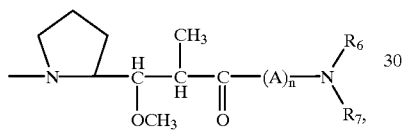

or a salt thereof with a pharmaceutically acceptable acid, wherein $R_1$–$R_5$ are each, independently, a hydrogen atom or a normal or branched $C_1$–$C_6$-alkyl group;

A is a methionyl, phenylalanyl or phenylglycyl residue;

n is 0 or 1;

$R_6$ is a hydrogen atom; and $R_7$ is selected from the group consisting of t-butyl, isopropyl, methyl, 2-pyridylmethyl, 3-pyridylmethyl, 4-pyridylmethyl, 2-(3-pyridyl)ethyl,

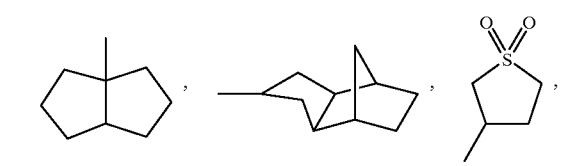

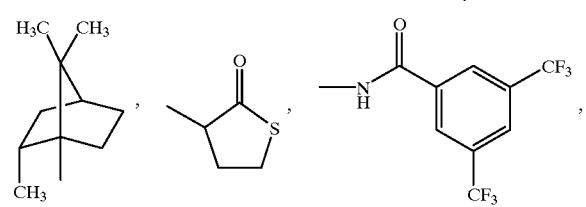

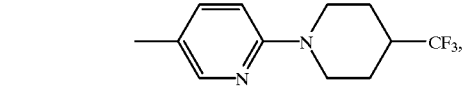

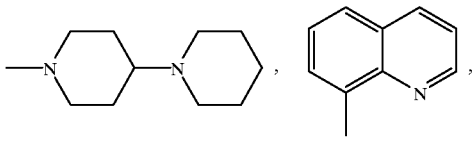

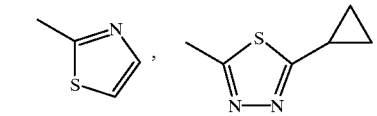

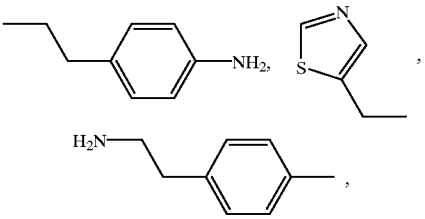

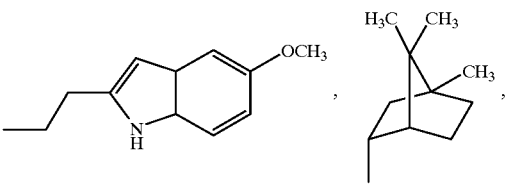

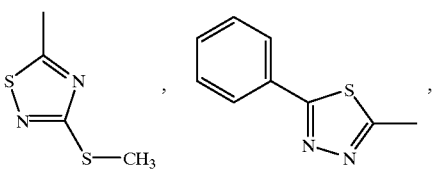

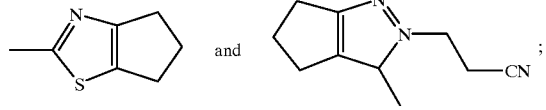

or $R_6$ is benzyl or —C(O)OR$_8$, wherein $R_8$ is a $C_1$–$C_6$-alkyl group; and $R_7$ is a 2-thiazolyl group.

15. The compound of claim 14 wherein $R_1$ and $R_2$ are each a methyl group, $R_3$ is an isopropyl or sec-butyl group, $R_4$ is an isopropyl, sec-butyl or isobutyl group, and $R_5$ is a sec-butyl group.

16. The compound of claim 14 wherein $R_1$ and $R_2$ are each methyl, $R_3$ and $R_4$ are each isopropyl, $R_5$ is sec-butyl, n is 0, $R_6$ is a hydrogen atom and $R_7$ is selected from the group consisting of t-butyl, isopropyl, methyl, 2-pyridylmethyl, 3-pyridylmethyl, 4-pyridylmethyl, 2-(3-pyridyl)ethyl,

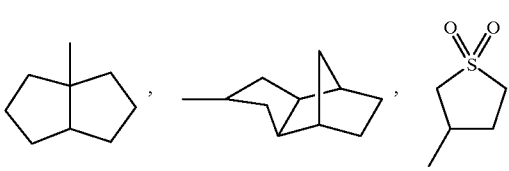

-continued
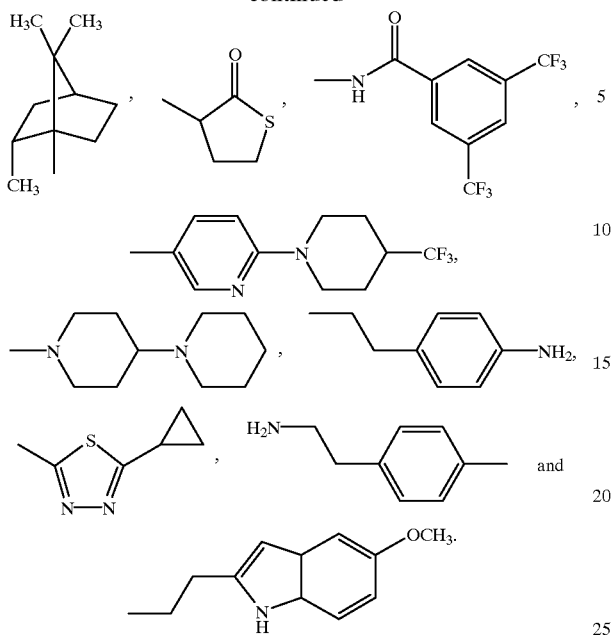
17. The compound of claim 14 wherein $R_1$ and $R_2$ are each methyl; $R_3$ is isopropyl; $R_4$ and $R_5$ are each sec-butyl; n is 0; $R_6$ is a hydrogen atom; and $R_7$ is
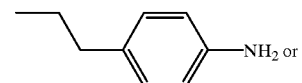
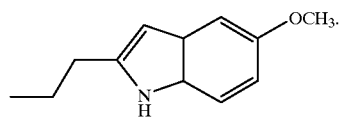
18. The compound of claim 14 wherein $R_1$ and $R_2$ are each methyl; $R_3$ is isopropyl; $R_4$ is isopropyl or sec-butyl; $R_5$ is sec-butyl; n is 0; $R_6$ is a benzyl group or —C(O)OCH$_3$; and $R_7$ is a 2-thiazolyl group.
* * * * *